(12) United States Patent
Morris

(10) Patent No.: US 9,308,193 B2
(45) Date of Patent: Apr. 12, 2016

(54) KINASE INHIBITORS FOR THE TREATMENT OF CANCER

(71) Applicant: PITNEY PHARMACEUTICALS PTY LIMITED, Kogarah, NSW (AU)

(72) Inventor: David Lawson Morris, Lugarno (AU)

(73) Assignee: PITNEY PHARMACEUTICALS PTY LIMITED, Nedlands, Western Australia (AU)

(*) Notice: Subject to any disclaimer, the term of this patent is extended or adjusted under 35 U.S.C. 154(b) by 0 days.

(21) Appl. No.: 14/387,270

(22) PCT Filed: Mar. 22, 2013

(86) PCT No.: PCT/AU2013/000290
§ 371 (c)(1),
(2) Date: Sep. 23, 2014

(87) PCT Pub. No.: WO2013/138863
PCT Pub. Date: Sep. 26, 2013

(65) Prior Publication Data
US 2015/0051290 A1 Feb. 19, 2015

(30) Foreign Application Priority Data
Mar. 23, 2012 (AU) ............... 2012901199

(51) Int. Cl.
*A61K 31/165* (2006.01)
*C07C 233/00* (2006.01)
*A61K 31/277* (2006.01)
*C07C 255/29* (2006.01)
*A61K 31/275* (2006.01)
*C07C 317/44* (2006.01)
*C07C 323/62* (2006.01)

(52) U.S. Cl.
CPC ............ *A61K 31/277* (2013.01); *A61K 31/275* (2013.01); *C07C 255/29* (2013.01); *C07C 317/44* (2013.01); *C07C 323/62* (2013.01)

(58) Field of Classification Search
USPC .......................................... 564/185; 514/617
See application file for complete search history.

(56) References Cited

U.S. PATENT DOCUMENTS 7,642,379 B2* 1/2010 Gauvry ................ C07C 255/26
564/185

FOREIGN PATENT DOCUMENTS

| CN | 102127074 | 7/2011 |
| WO | 2005044784 | 5/2005 |
| WO | WO 2005044784 A1 * | 5/2005 |

OTHER PUBLICATIONS

Pourgholami et al (Clinical Cancer Research vol. 12, pp. 1928-1935).*
Gusdon et al (American Journal of Obstetrics and Gynecology vol. 141, pp. 65-70, published 1981).*
Levandoski (European Journal of Pharmacology vol. 471, pp. 9-20, published 2003).*
Kaminsky and coworkers (Nature vol. 452, pp. 176-181, published 2008).*
Cecil's Textbook of Medicine, 21th Ed. Published 2000.*
Marone et al (International Journal of Cancer, vol. 75, pp. 34-39, 1998).*
Pourgholami et al (Clinical Cancer Research vol. 12 pp. 1928-1935 2006).*
Gusdon et al (Am. J. Obstet Gynecol. vol. 141 pp. 65-71, 1981).*
Pourgholami (Clinical Cancer Research vol. 12 pp. 1928-1935 2006).*
Gusdon (Am. J. Obstet Gynecol. vol. 141 pp. 65-71, 1981).*
International Application No. PCT/AU2013/000290, International Search Report mailed May 3, 2013.
Kaminsky, R. et al.: 'A new class of anthelmintics effective against drug-resistant nematodes' Nature vol. 452, No. 7184, 2008, pp. 176-180.
Ducray, P. et al.: 'Discovery of amino-acetonitrile derivatives, a new class of synthetic anthelmintic compounds' Bioorganic and Medicinal Chemistry Letters vol. 18, No. 9, 2008, pp. 2935-2938.
Kinsella, B. et al.: 'Determination of the anthelmintic monepantel and its sulfone metabolite in milk and muscle using a UHPLC-MS/MS and QuEChERS method' Journal of Chromatography, B: Analytical Technologies in the Biomedical and Life Sciences vol. 879, No. 31, 2011, pp. 3707-3713.
Guminska, M.: 'The Effect of Levamisole on Energy Metabolism in Ehrlich Ascites Tumour Cells in vitro' Biochemical Pharmacology vol. 35, No. 24, 1986, pp. 4369-4374.
European Patent Application No. EP13764613.9, Supplemental Search Report dated Aug. 5, 2015, 6 pages.
New Zealand Application No. 630807, First Examination Report dated Jun. 17, 2015, 2 pages.
Chinese Patent Application 201380024851.3, Office Action dated Sep. 6, 2015, 4 pages, no English translation available.
Armengol et al., "4E-binding protein 1: a key molecular "funnel factor" in human cancer with clinical implications", Cancer research 67.16 (2007): 7551-7555.
Australian Pesticides, Australian Pesticides and Veterinary Medicines Authority: "Public Release Summary on the Evaluation of the New Active Monepantel in the Product Zolvix Monepantel Broad Spectrum Oral Anthelmintic for Sheep" (2010).

(Continued)

*Primary Examiner* — Paul Zarek
*Assistant Examiner* — George W Kosturko
(74) *Attorney, Agent, or Firm* — Kilpatrick Townsend & Stockton LLP

(57) ABSTRACT

The present invention relates to kinase inhibitors for the treatment of cancer. Specifically, the present invention relates to the use of aminoactonitrile derivatives (AADs) in the treatment of cancer.

20 Claims, 24 Drawing Sheets

(56) References Cited

OTHER PUBLICATIONS

Bahrami et al., "Monepantel induces autophagy in human ovarian cancer cells through disruption of the mTOR/p70S6K signalling pathway", American journal of cancer research 4.5 (2014): 558.

Devita, Jr. et al., "A History of Cancer Chemotherapy", Cancer Res 2008; 68: (21). Nov. 1, 2008.

Králová et al., "Antiproliferative effect of benzimidazole anthelmintics albendazole, ricobendazole, and flubendazole in intestinal cancer cell lines", Anti-cancer drugs 24.9 (2013): 911-919 (abstract only).

Morris et al., "Pilot study of albendazole in patients with advanced malignancy. Effect on serum tumor markers/high incidence of neutropenia", Oncology 61.1 (2001): 42-46 (abstract only).

Nishikawa et al., "Significance of 4E-binding protein 1 as a therapeutic target for invasive urothelial carcinoma of the bladder", Urologic Oncology: Seminars and Original Investigations. vol. 33. No. 4. Elsevier, 2015.

Nygren et al., "Repositioning of the anthelmintic drug mebendazole for the treatment for colon cancer", Journal of cancer research and clinical oncology 139.12 (2013): 2133-2140.

Pourgholami et al., "Phase I clinical trial to determine maximum tolerated dose of oral albendazole in patients with advanced cancer", Cancer Chemother Pharmacol 65 (2010): 597-605.

Rufener et al., "Monepantel allosterically activates DEG-3/DES-2 channels of the gastrointestinal nematode Haemonchus contortus", Molecular pharmacology 78.5 (2010): 895-902.

* cited by examiner

A2780 cell treated 72h
with 25 µM MLP

U87 Glioma cells
treated with MPL-SO2

**** P value: <0.0001
*** P value: 0.0003
No star P value: 0.0699

KINASE INHIBITORS FOR THE TREATMENT OF CANCER

PRIOR RELATED APPLICATIONS

This application is a U.S. national phase patent application under 35 U.S.C. 371 of International Patent Application No. PCT/AU2013/000290, filed Mar. 22, 2013, which claims the benefit of priority to the Australian application serial number 2012901199 filed Mar. 23, 2012, each of which is incorporated herein by reference in its entirety.

TECHNICAL FIELD

In general, the present invention relates to kinase inhibitors for the treatment of cancer. Specifically, the present invention relates to the use of aminoactonitrile derivatives (AADs) in the treatment of cancer.

BACKGROUND

Aminoacetonitrile derivatives (AADs) are a class of anthelmintics effective against drug-resistant nematodes. The nematodes, or roundworms, comprise a large number of pathogens of man and domestic animals. Gastrointestinal nematodes, such as *Haemonchus contortus*, are major parasites of ruminants that cause substantial economic losses to livestock production worldwide.

Monepantel (MPL) (N-[(1S)-1-cyano-2-(5-cyano-2-trifluoromethyl-phenoxy)-1-methyl-ethyl]-4-trifluoromethyl-sulfanyl-benzamide) is an example of such an AAD and has been approved as a nematocide for the treatment of sheep gastrointestinal parasites.

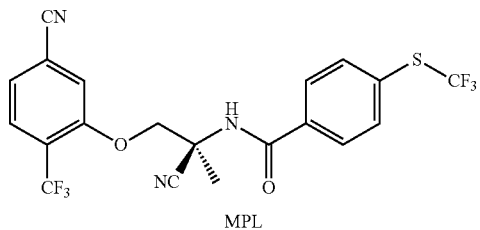 [SMILES: C[C@](C#N)(COc1cc(C#N)ccc1C(F)(F)F)NC(=O)c1ccc(SC(F)(F)F)cc1]

MPL

MPL has been shown to be efficacious against various species of livestock-pathogenic nematodes.

As a nematocide, MPL affects ligand-gated ion channels leading to interference of signal transduction at neuromuscular synapse. The affected parasites will then experience dysregulation in muscle contraction, paralysis, necrosis and moulting defects. Three nicotinic acetylcholine receptor (nAChR) related genes have been identified as the primary targets of MPL and all of the three genes encode for the proteins representing the DEG-3 subfamily of nAChR subunits that are only present in nematodes. The DEG-3 gene encodes a nAChR α-subunit which holds resemblance to that of α7 subunit in second transmembrane domain.

It has now surprisingly been found that AADs are also effective in the treatment of cancers. One of the greatest challenges in medicine during that past 50 years has been the identification of drugs that can effectively kill tumour cells without harming normal tissues. The side-effect profile of almost all known classes of anticancer drug is substantive in limiting the physician's ability to treat the cancer patient, especially at late stages when resistance to the drug often develops. Although other antihelminthic drugs such as benzimidazoles have been known to be effective in controlling the growth and development of cancerous cells, the surprising anti-cancer activity and low toxicity of compounds of formula (I), such as MPL, allows more flexible dosing regimens for cancer therapy with limited side effects.

SUMMARY OF THE INVENTION

According to a first aspect of the present invention there is provided a method for the treatment of one or more cancers, the method comprising administering a therapeutically effective amount of a compound of formula (I):

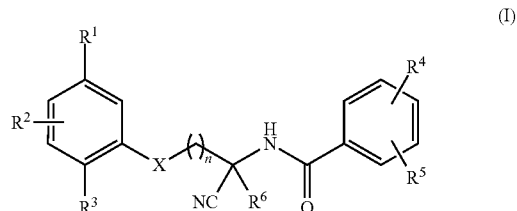

or a metabolite, pharmaceutically acceptable salt, solvate or prodrug thereof to a patient in need thereof, wherein $R^1$, $R^2$ and $R^3$ and $R^5$ are each independently selected from H, alkyl, halogen, —$CF_3$ or —CN;

$R^4$ and $R^6$ are each independently selected from H, alkyl, halogen, alkoxy, —$CF_3$, —$OCF_3$, —$SO_2CF_3$, —$SOCF_3$, or —S—$CF_3$;

X is heteroatom, N(alkyl) or NH; and n is 1 to 20.

Preferably, $R^1$ is —CN, H or halogen. More preferably, $R^1$ is —CN. Preferably, $R^2$ is H or halogen. More preferably, $R^2$ is H. Preferably, $R^3$ is —$CF_3$ or halogen. More preferably, $R^3$ is —$CF_3$. Preferably, $R^4$ is —S—$CF_3$, —$SOCF_3$, —$SO_2CF_3$, —$OCF_3$ or —$CF_3$. More preferably, $R^4$ is —S—$CF_3$ or —$SO_2CF_3$. Preferably, $R^5$ is H. Preferably, X is O. Preferably, n is 1 to 15, 1 to 10, 1 to 5, 1 to 2, or 1. More preferably, n is 1. Preferably, $R^4$ is arranged para to the amide moiety.

The compound of formula (I) may be the (R)- or (S)-enantiomer or the racemate. Preferably, the compound of formula (I) is the (S)-enantiomer.

Preferably, the compound of formula (I) is selected from any one of the following compounds:

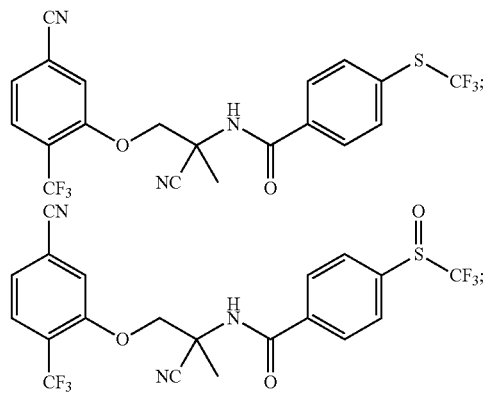

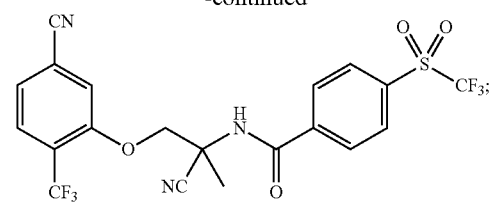

AAD 450

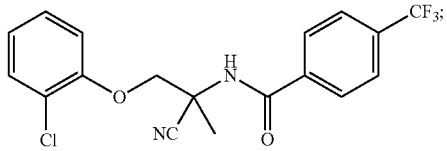

AAD 907

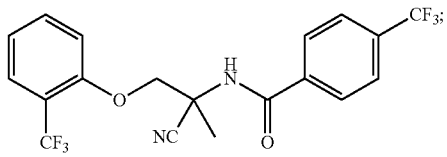

AAD 970

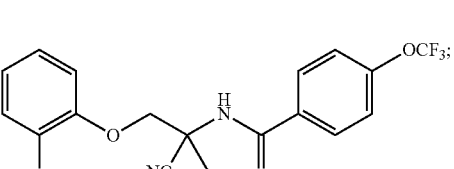

AAD 1154

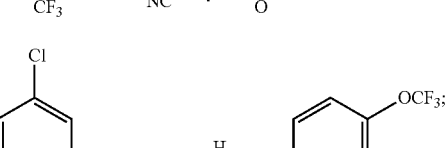

AAD 004

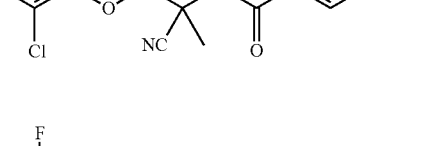

AAD 2009

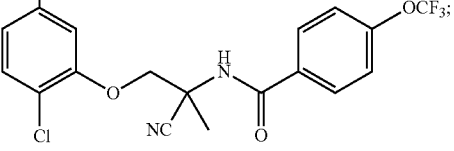

AAD 1336

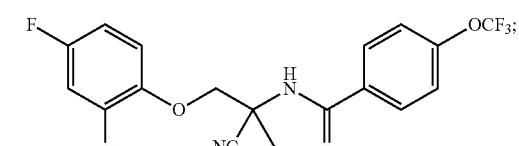

or

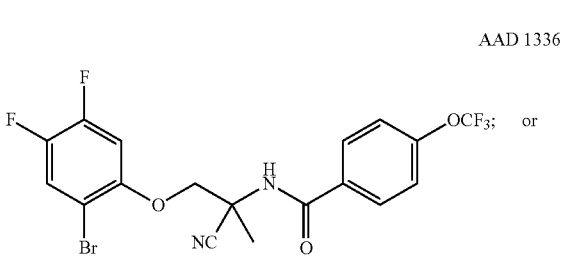

AAD 1470 wherein each of the above compounds is the (R)- or (S)-enantiomer, or the racemate, or a metabolite, pharmaceutically acceptable salt, solvate or prodrug thereof.

Preferably, the compound of formula (I) is MPL (N-[(1S)-1-cyano-2-(5-cyano-2-trifluoromethyl-phenoxy)-1-methyl-ethyl]-4-trifluoromethylsulfanyl-benzamide):

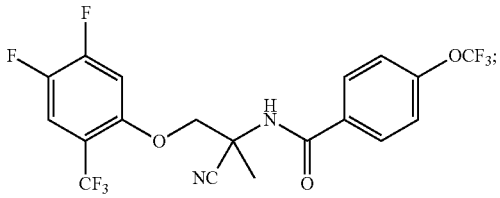

MPL or a metabolite, pharmaceutically acceptable salt, solvate or prodrug thereof.

Preferably, the compound of formula (I) is monepantel sulphone (MPL-SO2):

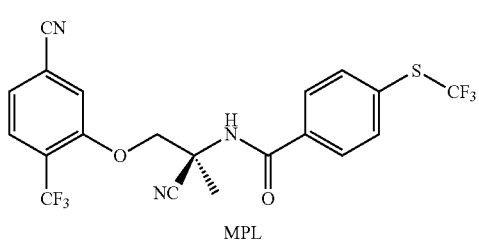 [SMILES: C[C@](C#N)(COc1cc(C#N)ccc1C(F)(F)F)NC(=O)c1ccc(SC(F)(F)F)cc1]

MPL-SO2 or a metabolite, pharmaceutically acceptable salt, solvate or prodrug thereof.

Further preferably, the compound of formula (I) is selected from any one of the following compounds:

AAD 2224

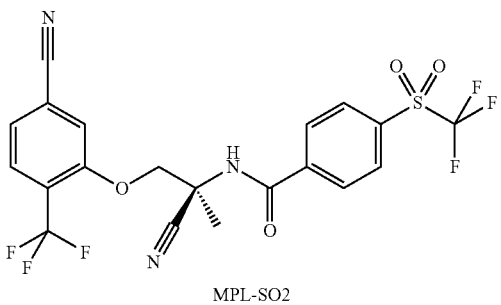 [SMILES: C[C@](C#N)(COc1cc(C#N)ccc1C(F)(F)F)NC(=O)c1ccc(S(=O)(=O)C(F)(F)F)cc1 ; "MPL-SO2"]

(MPL-(R))

-continued

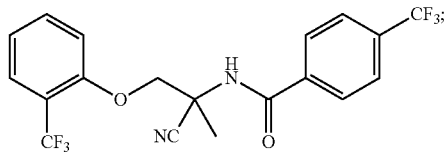
AAD 907

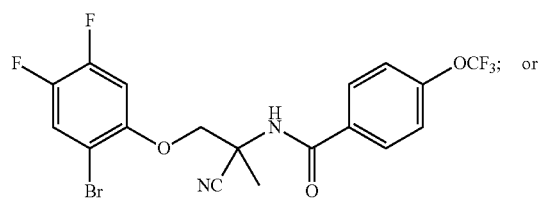
AAD 1336

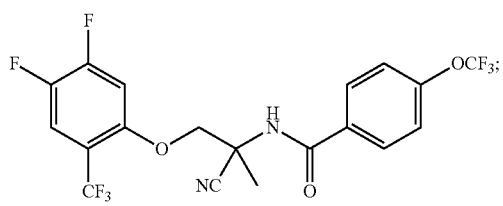
AAD 1470 or a metabolite, pharmaceutically acceptable salt, solvate or prodrug thereof.

Preferably, the cancer is associated with a kinase.

Preferably, the kinase is a cyclin-dependent kinase, and more preferably, $cdk_2$ or $cdk_4$.

Preferably, the cancer associated with a kinase is selected from the following: carcinoma, including that of the bladder, breast, colon, mesothelioma, kidney, liver, lung, including small cell lung cancer, non-small cell lung cancer, head and neck, oesophagus, gall bladder, ovary, pancreas, stomach, cervix, thyroid, prostate, and skin, including squamous cell carcinoma; hematopoietic tumors of lymphoid lineage, including leukaemia, acute lymphocytic leukaemia, acute lymphoblastic leukaemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocyte leukemia; tumors of mesenchymal origin, including liposarcoma, GIST, fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Preferably, the cancer to be treated is selected from cancer of the ovaries, breast, prostate or mesothelioma cancer, and most preferably the cancer to be treated is cancer of the ovaries.

In a second aspect of the invention, there is provided the use of a compound of formula (I) or a metabolite, pharmaceutically acceptable salt, solvate or prodrug thereof in the manufacture of a medicament for the treatment of one or more cancers associated with a kinase:

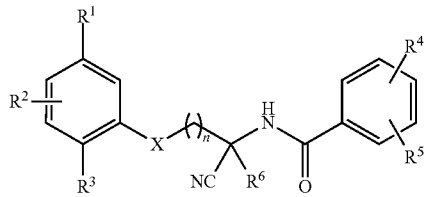

wherein
$R^1$, $R^2$ and $R^3$ and $R^5$ are each independently selected from H, alkyl, halogen, —$CF_3$ or —CN;
$R^4$ and $R^6$ are each independently selected from H, alkyl, halogen, alkoxy, —$CF_3$, —$OCF_3$, —$SO_2$—$CF_3$, —SO—$CF_3$ or —S—$CF_3$;
X is heteroatom, N(alkyl) or NH; and
n is 1 to 20.

In a third aspect of the invention, there is provided a compound of formula (I) or a metabolite, pharmaceutically acceptable salt, solvate or prodrug thereof, for use in the treatment of one or more cancers associated with a kinase:

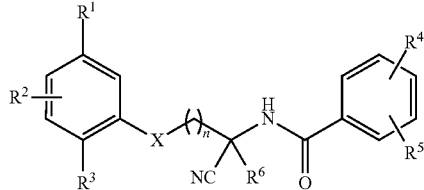

wherein
$R^1$, $R^2$ and $R^3$ and $R^5$ are each independently selected from H, alkyl, halogen, —$CF_3$ or —CN;
$R^4$ and $R^6$ are each independently selected from H, alkyl, halogen, alkoxy, —$CF_3$, —$OCF_3$, —$SO_2$—$CF_3$, —SO—$CF_3$ or —S—$CF_3$;
X is heteroatom, N(alkyl) or NH; and
n is 1 to 20.

μM) for 24, 48 or 72 h causes cleavage of PARP, which leads to cellular disassembly and serves as a marker of dying cells.

Figure 19:
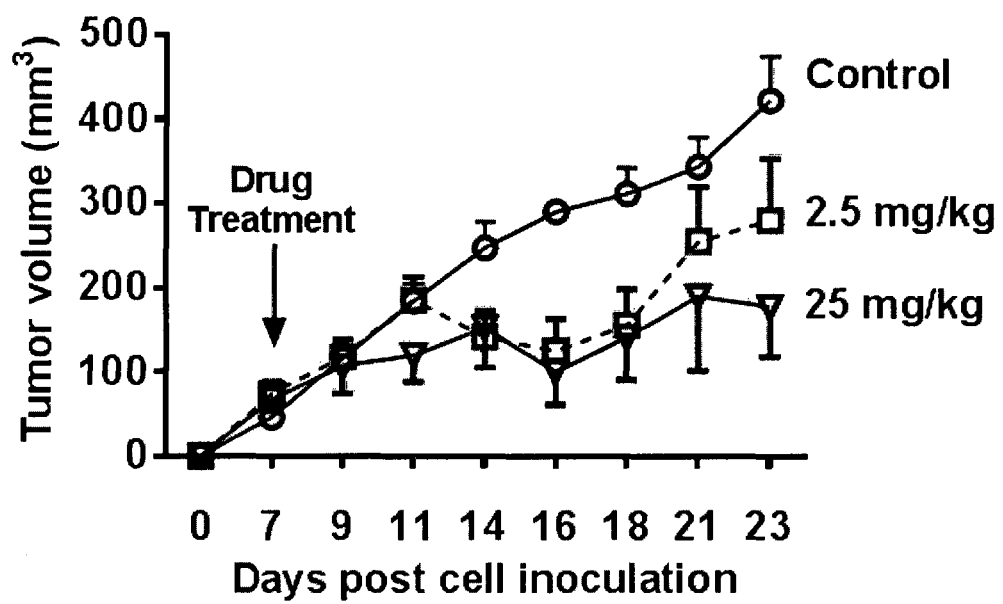

FIG. 19 shows the effect of i.p. (intraperitoneal) administered monepantel on s.c. (subcutaneous) tumor growth in nude mice. 2.5 million log-phase growing OVCAR-3 cells were injected s.c. into the left flank of each mouse. Tumor growth was monitored by caliper measurements and tumor volumes were determined through measuring orthogonal diameters. Estimated tumor volume was calculated based on the formula 1/2 (Length×Width$^2$), where width is the shorter of the two orthogonal measurements. Treatment was initiated 7 days post tumor cell injection before which, mice were randomized and assigned to treatment or the control group (6 per group). Monepantel suspended in 0.5% HPMC was administered i.p. at 2.5 or 25 mg/kg thrice weekly. Control group were treated with the vehicle only.

Figure 20:
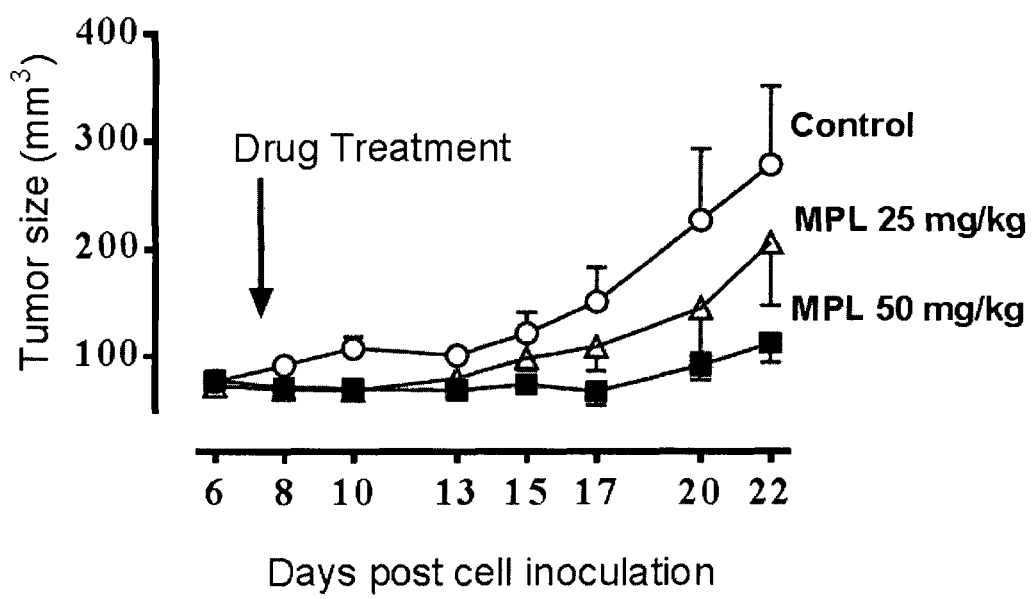

FIG. 20 shows the effect of i.p. administered monepantel on s.c. tumor growth in nude mice. Log-phase growing OVCAR-3 cells were injected s.c. into the left flank of each mouse. Tumor growth was monitored by caliper measurements and tumor volumes were determined through measuring orthogonal diameters. Estimated tumor volume was calculated based on the formula 1/2 (Length×Width$^2$), where width is the shorter of the two orthogonal measurements. Treatment was initiated 7 days post tumor cell injection before which, mice were randomized and assigned to treatment or the control group (6 per group). Monepantel suspended in 0.5% HPMC was administered i.p. at 25 or 50 mg/kg thrice weekly. Control group were treated with the vehicle only.

Figure 21:
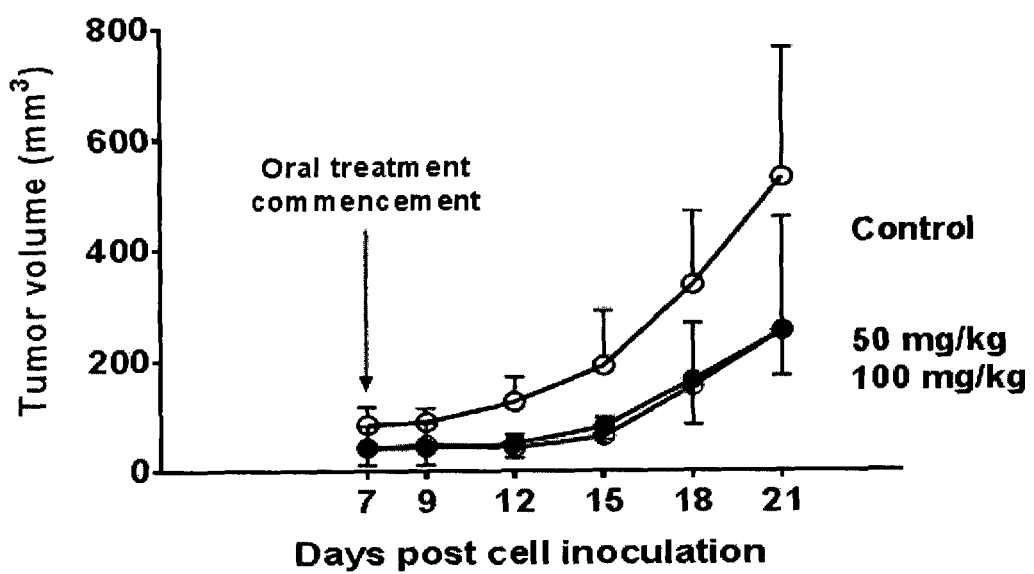

FIG. 21 shows the effect of oral monepantel on tumor growth in nude mice. OVCAR-3 cells were injected s.c. into the left flank of each mouse. Tumor growth was monitored by caliper measurements and tumor volumes were determined of orthogonal diameters, and the estimated tumor volume was calculated based on the formula 1/2 (Length×Width$^2$), where width is the shorter of the two orthogonal measurements. Treatment was initiated 7 days post tumor cell injection before which, mice were randomized and assigned to treatment or the control group (6 per group). Monepantel suspended in 0.5% HPMC was administered orally (100 μL) at 50 or 100 mg/kg thrice weekly. Control group were treated orally with the vehicle only.

FIGS. 19-21 in general show the effect of MPL on s.c. xenografts in female nude mice. Mice were inoculated in the left flank with 2.5 million log-phase growing human OVCAR-3 cells. Tumor growth was monitored by caliper measurements and tumor volumes were determined through measuring orthogonal diameters. Estimated tumor volume was calculated based on the formula 1/2 (Length×Width$^2$), where width is the shorter of the two orthogonal measurements. Treatment was initiated 7 days post tumor cell injection before which, mice were randomized and assigned to treatment or the control group (5-6 per group). Monepantel suspended in 0.5% HPMC was administered i.p. at 2.5 or 25 mg/kg (FIG. 19), 25 and 50 mg/kg (FIG. 20) or orally at 50 and 100 mg/kg, all given three times weekly. Control group mice received similar volume of 0.5% HPMC in an exactly similar manner and time.

Figure 22:
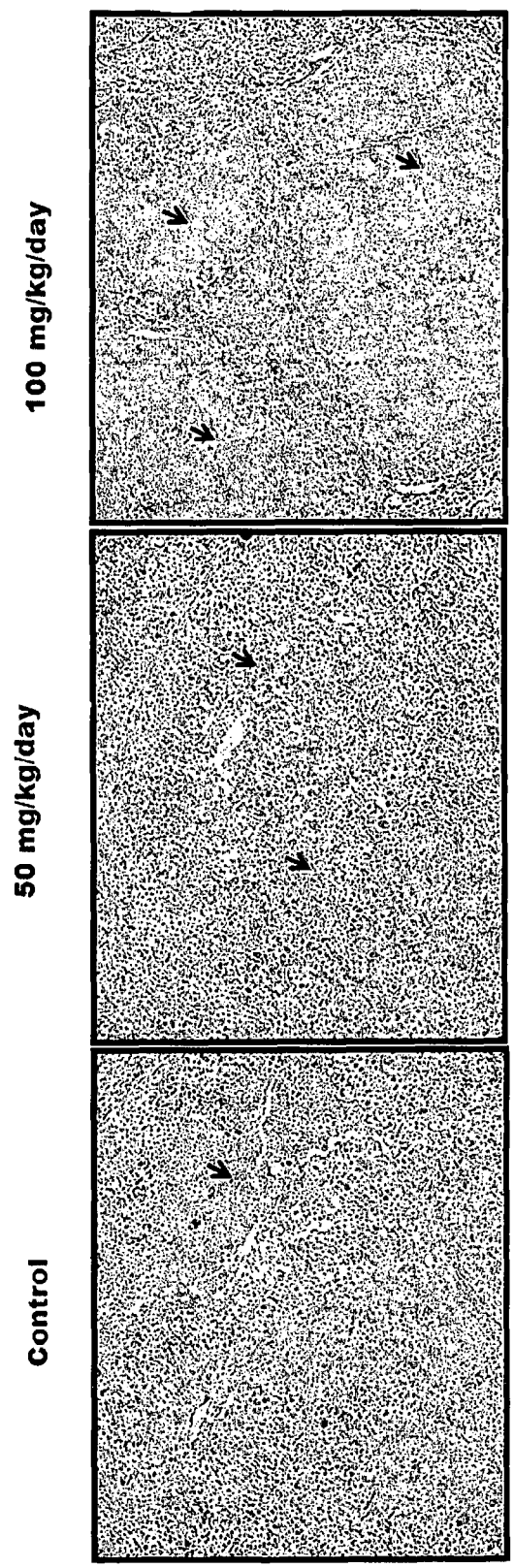

FIG. 22 shows how MPL induces necrosis in tumor tissues. Tumor tissue from subcutaneous xenografts in nude mice were treated with MPL administered orally on alternate days at 50 or 100 mg/kg/day. Histological images of tumors are shown in hematoxylin and eosin staining (H&E; top row), indicating profound drug-induced necrosis (black arrow head; magnification ×10). A representative image of tumor histology from tumors excised from MPL treated mice demonstrating extensive necrosis at the higher dose of 100 mg/kg (s.c. tumor, oral treatment, ×3 weekly for 2 weeks).

DEFINITIONS

"Halogen" means fluorine, chlorine, bromine or iodine, preferably fluorine or chlorine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Heteroatom" means an atom selected from N, O, P and S. Where necessary, any undesignated valency is independently selected from H, OH, carbonyl, n-alkyl or alkoxy.

"n" may be 1 to 20, preferably 1 to 10, more preferably 1 to 6, and most preferably 1 to 4.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluene sulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flow ability and solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options, meaning that more than one substituent may be present simultaneously at various sites.

"Prodrugs" and "solvates" of the compounds of the invention are also contemplated herein. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of formula (I) or a metabolite, pharmaceutically acceptable salt or solvate of the compound. The transformation may occur by various mechanisms (e.g., by metabolic or chemical processes). A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

"Metabolites" of the compounds of the invention refer to the intermediates and products of metabolism.

The compounds of formula (I) may contain asymmetric or chiral centres, and, therefore, exist in different stereoisomeric forms. It is intended that all stereoisomeric forms of the compounds of formula (I) as well as mixtures thereof, including racemic mixtures, form part of the present invention. In addition, the present invention embraces all geometric and positional isomers. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolysing) the individual diastereomers to the corresponding pure enantiomers. Enantiomers can also be separated by use of chiral HPLC column. The chiral centres of the present invention can have the S or R configuration as defined by the IUPAC 1974.

The use of the terms "salt", "solvate", or "prodrug" and the like, is intended to equally apply to the salt, solvate and prodrug of enantiomers, stereoisomers, rotamers, tautomers, positional isomers, racemates or prodrugs of the inventive compounds.

As used in this application, the singular form "a", "an" and "the" include plural references unless the context clearly dictates otherwise.

As used herein, the term "comprising" means "including." Variations of the word "comprising", such as "comprise" and "comprises," have correspondingly varied meanings. Thus, for example, a pharmaceutical composition "comprising" a compound of formula (I) may consist exclusively of that compound or may include one or more additional components (e.g. a pharmaceutically acceptable carrier, excipient and/or diluent).

As used herein the term "plurality" means more than one. In certain specific aspects or embodiments, a plurality may mean 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or more, and any integer derivable therein, and any range derivable therein.

"Therapeutically effective amount" means an amount of at least one compound of formula (I), or a metabolite, pharmaceutically acceptable salt, solvate or prodrug thereof, that substantially inhibits proliferation and/or prevents differentiation of a human tumor cell, including human tumor cell lines. The term "therapeutically effective amount" as used herein, includes within its meaning a non-toxic but sufficient amount of an agent or composition for use in the present invention to provide the desired therapeutic effect. The exact amount required will vary from subject to subject depending on factors such as the species being treated, the age and general condition of the subject, the severity of the condition being treated, the particular agent being administered, the mode of administration and so forth. Thus, it is not possible to specify an exact "effective amount" applicable to all embodiments. However, for any given case, an appropriate "effective amount" may be determined by one of ordinary skill in the art using only routine experimentation.

DETAILED DESCRIPTION

The AADs (e.g. formula (I)) are a class of compounds that may be synthesized using the ordinary knowledge of organic synthetic methodology. For example, the AADs may be synthesised by derivitisation of phenols with chloroacetone, Strecker reaction and acylation of the resultant amine with aroyl chlorides (as shown in Scheme 1). Where necessary, a particular enantiomer may then be obtained, for example, by chiral resolution (as shown in Scheme 2).

Scheme 1:

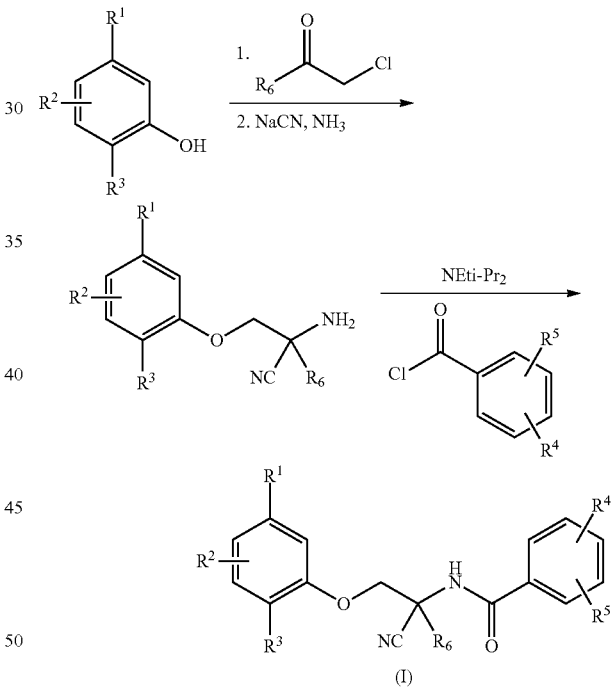

Scheme 2:

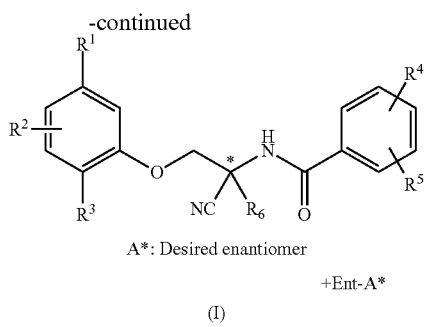

A*: Desired enantiomer

+Ent-A*

(I)

The AADs are a class of chemicals that have previously been used to treat drug-resistant nematodes. The compound, MPL, is an example of one such AAD that targets nicotinic acetylcholine receptors in nematodes, and has been used extensively for the treatment of parasites in ruminants.

Surprisingly, the present inventors have found that compounds of formula (I), such as MPL and MPL-SO2, have anti-cancer activity. More specifically, compounds of formula (I), including MPL and MPL-SO2, have been shown to inhibit cell proliferation and colony formation of cancer cell lines. For example, ovarian cancer cell lines have shown to be very sensitive to compounds of formula (I), and it is evident that other cell lines are also highly sensitive. These include breast cancer, mesothelioma, prostate cancer and glioblastoma cell lines. MPL is very effective against chemo-resistant, androgen insensitive PC-3 and DU 145 prostate cancer cells. Similarly, replication of PET and YOU cells (mesothelioma) and U87 cells (glioblastoma), which are also highly resistant to chemotherapy, are profoundly suppressed by MPL.

Not wishing to be bound by theory, it is surprising that, unlike the mode of action seen in nematodes, the compounds of formula (I) may act by targeting cyclin-dependent kinases in cancer cell lines. More specifically, the compounds of formula (I) appear to interfere with the cell-cycle regulatory kinases, such as cyclin-dependent kinase 2 ($Cdk_2$) and cyclin-dependent kinase 4 ($Cdk_4$).

The treatment of cancer cell lines with compounds of formula (I), such as MPL and MPL-SO2, appears to result in cell cycle-arrest. Again not wishing to be bound by theory, but it appears that treatment may induce a G1 cell cycle arrest, as evidenced by the accumulation of cells in the G1 phase of the cell cycle. Furthermore, it is suggested that that the treatment of cancer cell lines with compounds of formula (I), such as MPL and MPL-SO2, may induce an irreversible $G_0$ cell cycle arrest, as evidenced by the cells exiting the cell cycle and undergoing autophagy and/or apoptosis. This new class of antihelminthic agents may present a different mechanistic profile than benzimidazoles offering a new improved approach to cancer therapy.

Compositions, Medicaments and Kits

The present invention provides pharmaceutical compositions, medicaments and kits which comprise at least one compound of formula (I), or a metabolite, pharmaceutically acceptable salt, solvate or prodrug of said compound and at least one pharmaceutically acceptable carrier. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions, for example water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen. Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably, the compound of formula (I) is administered orally.

Compositions and medicaments of the present invention may comprise a pharmaceutically acceptable carrier, adjuvant, excipient and/or diluent. The carriers, diluents, excipients and adjuvants must be "acceptable" in terms of being compatible with the other ingredients of the composition or medicament, and are generally not deleterious to the recipient thereof. Non-limiting examples of pharmaceutically acceptable carriers or diluents are demineralised or distilled water; saline solution; vegetable based oils such as peanut oil, safflower oil, olive oil, cottonseed oil, maize oil; sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxylpropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrolidone; agar; gum tragacanth or gum acacia, and petroleum jelly. Typically, the carrier or carriers will form from about 10% to about 99.9% by weight of the composition or medicament.

Composition and medicaments of the present invention may be in a form suitable for administration by injection (e.g. for parenteral administration including subcutaneous, intramuscular or intravenous injection), by oral administration (such as capsules, tablets, caplets, and elixirs, for example), by topical administration (e.g. in the form of an ointment, cream or lotion, or a form suitable for delivery as an eye drop), or by intranasal inhalation (e.g. in the form of aerosols).

For administration as an injectable solution or suspension, non-toxic parenterally acceptable diluents or carriers can include, Ringer's solution, isotonic saline, phosphate buffered saline, ethanol and 1,2 propylene glycol. Methods for preparing parenterally administrable compositions and medicaments are apparent to those of ordinary skill in the art, and are described in more detail in, for example, Remington's Pharmaceutical Science, 15th ed., Mack Publishing Company, Easton, Pa.

For oral administration, some examples of suitable carriers, diluents, excipients and adjuvants include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl stearate which delay disintegration. Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending, agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Formulations for oral administration may comprise one or more emulsifying agents. Suitable emulsifying agents include dispersing agents as exemplified above or natural gums such as guar gum, gum acacia or gum tragacanth.

Topical formulations of the present invention may comprise an active ingredient together with one or more acceptable carriers, and optionally any other therapeutic ingredients. Formulations suitable for topical administration include liquid or semi-liquid preparations suitable for penetration through the skin to the site where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil, wool fat or its derivatives, or a fatty acid such as stearic or oleic acid together with an alcohol such as propylene glycol or macrogols.

Compositions and medicaments of the present invention may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

Compositions and medicaments of the present invention may be administered in the form of a liposome. Suitable methods to form liposomes are known in the art, and in relation to this specific reference is made to Prescott, (Ed), (1976), "*Methods in Cell Biology*", Volume XIV, Academic Press, New York, N.Y. p. 33 et seq.

Supplementary active ingredients such as adjuvants or biological response modifiers can also be incorporated into compositions and medicaments of the present invention.

Any suitable adjuvant may be included in compositions and medicaments of the present invention. For example, an aluminium-based adjuvant may be utilised. Suitable aluminium-based adjuvants include, but are not limited to, aluminium hydroxide, aluminium phosphate and combinations thereof. Other specific examples of aluminium-based adjuvants that may be utilised are described in European Patent No. 1216053 and U.S. Pat. No. 6,372,223. Other suitable adjuvants include Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminium salts such as aluminium hydroxide gel (alum) or is aluminium phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; oil in water emulsions including those described in European Patent No. 0399843, U.S. Pat. No. 7,029,678 and PCT Publication No. WO 2007/006939; and/or additional cytokines, such as GM-CSF or interleukin-2, -7, or -12, granulocyte-macrophage colony-stimulating factor (GM-CSF), monophosphoryl lipid A (MPL), cholera toxin (CT) or its constituent subunit, heat labile enterotoxin (LT) or its constituent subunit, toll-like receptor ligand adjuvants such as lipopolysaccharide (LPS) and derivatives thereof (e.g. monophosphoryl lipid A and 3-Deacylated monophosphoryl lipid A), muramyl dipeptide (MDP) and F protein of Respiratory Syncytial Virus (RSV).

Another aspect of this invention is a kit comprising a therapeutically effective amount of at least one compound of formula (I), or a metabolite, pharmaceutically acceptable salt, solvate or prodrug of said compound and a pharmaceutically acceptable carrier, vehicle or diluent.

Another aspect of this invention is a kit comprising an amount of at least one compound of formula (I), or a metabolite, pharmaceutically acceptable salt, solvate or prodrug of said compound and an amount of at least one anticancer therapy and/or anti-cancer agent listed above, wherein the amounts of the two or more ingredients result in desired therapeutic effect.

Kits of the present invention may comprise components to assist in performing the methods of the present invention such as, for example, administration device(s), buffer(s), and/or diluent(s). The kits may include containers for housing the various components and instructions for using the kit components in the methods of the present invention.

In certain embodiments, the kits may be combined kits.

In other embodiments, the kits may be fragmented kits.

Dosages and Routes of Administration

The agents, compositions and medicaments can be administered to a recipient by standard routes, including, but not limited to, parenteral (e.g. intravenous, intraspinal, subcutaneous or intramuscular), oral, topical, or mucosal routes (e.g. intranasal). In some embodiments, they may be administered to a recipient in isolation or in combination with other additional therapeutic agent(s). In such embodiments the administration may be simultaneous or sequential.

In general, the agents, compositions and medicaments can be administered in a manner compatible with the route of administration and physical characteristics of the recipient (including health status) and in such a way that the desired effect(s) are induced (i.e. therapeutically effective, immunogenic and/or protective). For example, the appropriate dosage may depend on a variety of factors including, but not limited to, a subject's physical characteristics (e.g. age, weight, sex), whether the agent, composition or medicament is being used as single agent or adjuvant therapy, the progression (i.e. pathological state) of the cancer being treated, and other factors readily apparent to those of ordinary skill in the art.

Various general considerations when determining an appropriate dosage of the agents, compositions and medicaments are described, for example, in Gennaro et al. (Eds) (1990), "*Remington's Pharmaceutical Sciences*", Mack Publishing Co., Easton, Pa., USA; and Gilman et al., (Eds), (1990), "*Goodman And Gilman's: The Pharmacological Bases of Therapeutics*", Pergamon Press.

A surprising advantage of the present invention is that compounds of formula (I) generally reflect a low toxicity. For example, MPL has single-dose toxicity in excess of 2000 mg per kg of body weight. As such, an agent, composition or medicament for use in the present invention may be administered to a patient as a single dose of an amount of up to and including 2000 mg of active component(s) per kg of body weight. Moreover, another surprising advantage of using the present invention for the treatment of cancer is the generally high clinical tolerance of compounds of formula (I). For example, a dosage of 1000 mg of MPL per kg of body weight per 24 hours is well tolerated in mammals. As such, an agent, composition or medicament for use in the present invention may be administered to a patient in an amount of up to and including 1000 mg of active component(s) per kg of body weight per 24 hours.

Generally, an effective dosage is expected to be in the range of about 0.0001 mg to about 1000 mg of active component(s) per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; or about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; or about 5.0 mg to about 15 mg per kg body weight per 24 hours.

For example, a preferred dosage may be about 10-100 mg of the compound of formula (I) per kg of body weight per 24 hours. Further, a preferred dosage may be about 50 mg of a compound of formula (I) per kg of body weight per 24 hours.

Typically, in treatment applications, the treatment may be for the duration of the cancer. Further, it will be apparent to one of ordinary skill in the art that the optimal quantity and spacing of individual dosages can be determined by the nature and extent of the disease state or condition being treated, the form, route and site of administration, and the nature of the particular subject being treated. Optimum dosages can be determined using conventional techniques.

In many instances (e.g. preventative applications), it may be desirable to have several or multiple administrations of an agent, composition or medicament of the present invention which may, for example, be administered 1, 2, 3, 4, 5, 6, 7, 8, 9, 10, or more times. The administrations may be from about one to about twelve week intervals, and in certain embodiments from about one to about four week intervals. Periodic re-administration is also contemplated.

It will also be apparent to one of ordinary skill in the art that the optimal course of administration can be ascertained using conventional course of treatment determination tests.

Where two or more entities (e.g. agents or medicaments) are administered to a subject "in conjunction", they may be administered in a single composition at the same time, or in separate compositions at the same time, or in separate compositions separated in time.

Certain embodiments of the present invention involve administration of the agents, compositions or medicaments in multiple separate doses. Accordingly, the methods for prophylactic and therapeutic treatment described herein encompass the administration of multiple separated doses to a subject, for example, over a defined period of time. Accordingly, in some embodiments the methods include administering a priming dose, which may be followed by a booster dose. The booster may be for the purpose of re-vaccination. In various embodiments, the agent, composition or medicament is administered at least once, twice, three times or more.

The agents, compositions and medicaments may generally be administered in an effective amount to achieve an intended purpose. More specifically, they may be administered in a therapeutically effective amount which means an amount effective to prevent development of, or to alleviate the existing symptoms of, a target disease or condition. Determination of effective amounts is well within the capability of persons of ordinary skill in the art. For example, a therapeutically effective dose of the agents, compositions and medicaments can be estimated initially from cell culture assays. For example, a dose can be formulated in animal models to achieve a circulating concentration range that includes the $IC_{50}$ as determined in cell culture. Such information can be used to more accurately determine useful doses in humans and other mammalian subjects.

A therapeutically effective dose refers to that amount of the agent, composition or medicament to prevent development of symptoms, ameliorate symptoms and/or prolong the survival of the subject under treatment. Toxicity and therapeutic efficacy of the agents, compositions and medicaments can be determined by standard pharmaceutical assays in cell cultures, and/or experimental animals (e.g. by determination of the $LD_{50}$ (the dose lethal to 50% of the population) and the $ED_{50}$ (the dose therapeutically effective in 50% of the population)). The dose ratio between toxic and therapeutic effects is the therapeutic index which can be expressed as the ratio between $LD_{50}$ and $ED_{50}$. Agents, compositions and medicaments which exhibit high therapeutic indices are preferred. The data obtained from such cell culture assays and/or animal studies may be used to formulate a range of dosage for use in humans or other mammals. The dosage of such compounds lies preferably within a range of circulating concentrations that include the $ED_{50}$ with little or no toxicity. The dosage may vary within this range depending upon the dosage form employed and the administration route utilised. The exact formulation, route of administration and dosage can be selected without difficulty by an individual physician in view of the subject's condition (see, for example, Fingl et al., (1975), in "*The Pharmacological Basis of Therapeutics*", Ch. 1 p. 1). Dosage amount and interval may be adjusted individually to provide plasma levels of the active agent sufficient to achieve and maintain the desired therapeutic effects and/or a minimal effective concentration (MEC). Dosages necessary to achieve the MEC will depend on the route of administration and other individual characteristics. Bioassays and/or HPLC assays may be used to determine plasma concentrations.

Dosage intervals may also be determined using MEC value. In general, the agents, compositions and medicaments may be administered using a regimen which maintains plasma levels above the MEC for between about 10%-90% of the time, preferably between 30%-90% and more preferably between about 50%-90%. In embodiments where local administration or selective uptake is utilised, the effective local concentration of the drug may not be related to plasma concentration.

The compounds of this invention may also be useful in combination (administered together or sequentially) with one or more of anti-cancer treatments such as radiation therapy, and/or one or more anti-cancer agents selected from the group consisting of cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™ (4~[2-[4-[(11R)-3,10-dibromo-8-chloro-6, 11-dihydro-5H-benzo[5,6]cyclohepta[1,2-b]pyridin-11-yl-]-1-piperidinyl]-2-oxoethyl]-1-piperidinecarboxamide, or SCH 66336 from Schering-Plough Corporation, Kenilworth, N.J.), tipifamib (Zamestra® or R115777 from Janssen Pharmaceuticals), L778.123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, lressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, Cytoxan, and gemcitabine.

Subjects

Prophylactic and therapeutic methods of the present invention may be applied to any suitable subject. In some embodiments, the subject is a mammalian subject. For example, the subject may be a mouse, rat, dog, cat, cow, sheep, horse or any other mammal of social, economic or research importance. Hence, the subject may be a mammal such as, for example, a human or a non-human mammal.

It will be appreciated by persons of ordinary skill in the art that numerous variations and/or modifications can be made to the present invention as disclosed in the specific embodiments without departing from the spirit or scope of the present invention as broadly described. The present embodiments are, therefore, to be considered in all respects as illustrative and not restrictive.

The present invention will now be described with reference to specific examples, which should not be construed as in any way limiting.

EXAMPLES

Materials and Methods

Cell Lines

The human ovarian cancer cell lines OVCAR-3, SKOV-3 and A2780 and primary cells human umbilical vein endothelial cells (HUVEC) and all other cell lines were obtained from the American Type Culture Collection (ATCC) and maintained according to their instructions. Astrocytes and glioma cell lines were kindly gifted by Dr. Kerry McDonald from Lowy Cancer Research Centre, University of New South Wales, Australia.

Cell Proliferation Assay

Cell proliferation was assessed using the sulforhodamine B (SRB) assay. Cells seeded in 96-well plate (2,000-3,000 cell/well) were treated with MPL (0, 1, 5, 10, 25, 50 and 100 µmol/L) for 72 h. Cells were then fixed, washed and stained with 100 µl of 0.4% (w/v) SRB dissolved in 1% acetic acid. Unbound dye was removed by five washes with 1% acetic acid before air drying. Bound SRB was solubilized with 100 µl of 10 mM Tris base (pH 10.5) and the absorbance read at 570 nm. Exactly the same procedure was used to assess MPL-SO2. Both agents were dissolved in ethanol and diluted with media to give the final concentrations required for cell culture assays.

Cell Viability Assay

For viability experiments, cells seeded in 6 well plates were exposed to monepantel (MPL) at 0, 1, 10, 50 and 100 µM concentrations for 24, 48 or 72 h. Monepantel (gift by Novartis, Basel, Switzerland) was dissolved in 100% ethanol and then diluted with the cell culture media. At the end of treatment period, cells were washed with PBS, trypsinized and counted using Trypan blue and hemocytometer. All experimental points were set up in quadruplicate and each experiment was performed at least twice.

Colony Formation Assay

For colony formation assay, $5 \times 10^6$ cells, such as OVCAR-3 or A2780 cells, were plated in 100 mm Petri dishes and allowed to attach overnight. Media were aspirated off and exponentially growing cells were incubated with various concentrations of MPL for 72 h. At this point, the medium was aspirated, the dishes were washed with PBS, and drug free medium was added to each plate. Media were changed twice weekly for 3 weeks. Following this, plates were gently washed with PBS and cells were fixed with 100% ethanol and stained with a 0.5% solution of filtered crystal violet. Colonies consisting of more than 50 cells were counted under an inverted microscope.

Cell Cycle Analysis

The effect of MPL on the cell cycle was determined using standard flow cytometry analysis protocols and procedures. Briefly, $0.7 \times 10^6$ million cells seeded in 25 cm$^3$ flasks and allowed to adhere overnight were treated with MPL for 24 or 48 h. Cells were collected with trypsinization and pooled with the cells floating in the medium. The cell suspensions were centrifuged, washed with PBS and fixed with methanol. Cells were then washed, resuspended in propodium iodide and ribonuclease A in PBS for 30 min at room temperature and analyzed by flow cytometry (Becton Dickinson FACSort).

Western Blot Analysis

Protein expression in cells was determined using western blot analysis. After treatment with the indicated concentrations of MPL, cell lysates were prepared and probed with antibodies for cdk2, cdk4, cyclin A, cyclin E, PARP-1 (1:1000 dilutions; Cell Signalling Technology), and p53 (1:200 dilutions; Santa Cruz Biotechnology). Comparable loading of proteins on the gel was verified by re-probing the blots with a GAPDH antibody (1:30000 dilutions; Sigma-Aldrich).

In Vivo Experiments

Female nude mice (6 weeks old) were purchased from Biological Resources (University of New South Wales). Institutional animal ethics approvals covered procedures carried out on mice. Briefly, $2.5 \times 10^6$ log-phase growing OVCAR-3 cells were injected s.c. into the left flank of each mouse. Animals were weighed once weekly while their tumor volumes were determined twice weekly. Tumor growth was monitored by caliper measurements of orthogonal diameters, and the estimated tumor volume was calculated based on the formula 1/2 (Length×Width$^2$), where width is the shorter of the two orthogonal measurements. Based on institutional ethics approval, mice were euthanized before the tumor volume reached 500 mm3. Treatment was initiated on day 8 post tumor cell inoculation when mice were randomized and assigned to one of MPL or vehicle treated groups (5-6 mice per group). MPL was suspended in hydroperoxy methylcellulose (0.5% w/v HPMC), sterilized by sonnicator and administered every other day either intraperitoneally (i.p) or orally as gavage (100 µL).

In the first pilot trial, the drug was administered i.p. at 2.5 or 25 mg/kg body weight, three times weekly for 2 weeks.

Following the outcome, in the next set of animals, the dose was increased to 25 and 50 mg/kg, three times weekly.

In the last (third) pilot study, mice were treated orally. The doses administered were 50 and 100 mg/kg three times weekly. In all these trials, mice in control groups received similar volume of the vehicle (0.5% HPMC). Tumor histology/immunohistochemistry was performed on formalin fixed tumor slices according to standard procedures.

Statistical Analysis

All data are reported as the mean±standard errors (S.E.M.) from at least two independent experiments. Differences in tumor volume between MPL treated versus control group were analysed using one way ANOVA with post hoc Dunnett test. Quantitative variables were compared using the Student's t test. Significant statistical difference was defined at $P<0.05$.

Results

MPL Inhibits Cell Proliferation

The effect of MPL was examined on the growth of ovarian cancer cell lines of OVCAR-3, A2780 and SKOV-3. By employing the SRB assay, the effect of MPL on cell proliferation was examined. MPL inhibited proliferation of OVCAR-3, A2780 and SKOV-3 cells in a concentration-dependent manner with IC$_{50}$ values of 6.3, 10.0 and 29.3 respectively, according to Table 1. It is evident from these results that ovarian cancer cell lines are sensitive to the anti-proliferative effects of MPL. SKOV-3 cells were the least sensitive. MPL-SO2 was also tested in a similar manner using the SRB proliferation assay. It was found that MPL-SO2 is as potent as MPL. MPL-SO2 reduced viability of cancer cell-lines growing in culture and inhibited cell proliferation. IC$_{50}$ values for MPL-SO2 are presented in Table 1.

The inhibitory effect of MPL on cell proliferation was also tested on a range of cells, such as breast, prostate and mesothelioma cells. Results obtained are presented in Table 1. Further results are presented in Table 2.

TABLE 1

IC$_{50}$ values for MPL and MPL-SO2 (72 h in vitro treatment, SRB assay)

| | | IC$_{50}$ (µM) | |
| --- | --- | --- | --- |
| Cell Lines | Type of cancer | MPL | MPL-SO2 |
| OVCAR-3 | Ovarian cancer | 6.3 | 5.5 |
| A2780 | Ovarian cancer | 10.0 | 4.2 |
| SKOV-3 | Ovarian cancer | 29.3 | 26 |
| IGROV-1 | Ovarian cancer | 6.1 | — |
| 1A9 | Ovarian cancer | 1.8 | 4.8 |
| T47-D | Breast cancer | 5.7 | — |
| MDA-MB-231 | Breast cancer | 24.0 | 23.6 |
| MCF-7 | Breast cancer | — | 7.3 |
| PET | Mesothelioma | 26.3 | — |
| YOU | Mesothelioma | 23.1 | — |
| PC-3 | Prostate cancer | 21.6 | — |
| DU-145 | Prostate Cancer | 23.5 | — |
| U87 | Glioblastoma | 26.2 | 20.5 |
| HUVEC | Human Umbilical Vein Endothelial Cells | 87.8 | 47.8 |
| CHO | Chinese Hamster Ovary | — | 73.7 |
| HEK | Human Embryonic Kidney | 50.5 | — |

TABLE 2

IC$_{50}$ values for MPL and MPL-SO2 in suppressing proliferation of various cancer cell lines.

| | | IC$_{50}$ (µM) | |
| --- | --- | --- | --- |
| Cell Line | Cell Type | MPL | MPL-SO2 |
| OVCAR-3 | Ovarian Cancer | 6.3 ± 0.8*** | 5.5 ± 1.3*** |
| A2780 | Ovarian Cancer | 10 ± 3.8** | 4.2 ± 2.1** |
| SKOV-3 | Ovarian Cancer | 31.18 ± 0.76*** | 26 |

TABLE 2-continued

IC$_{50}$ values for MPL and MPL-SO2 in suppressing proliferation of various cancer cell lines.

| Cell Line | Cell Type | IC$_{50}$ (µM) MPL | MPL-SO2 |
|---|---|---|---|
| IGROV-1 | Ovarian Cancer | 4.4 ± 0.27** | 4.4 ± 1.5** |
| 1A9 | Ovarian Cancer | 2.5 ± 0.45** | 3.42 ± 0.1** |
| T47-D | Breast Cancer | 5.3 ± 0.003** | 10.2 ± 0.6** |
| MDA-MB-231 | Breast Cancer | 23.8 ± 0.2** | 21.6 ± 7.5*** |
| MCF-7 | Breast Cancer | 15.4 ± 1.1** | 8.0 ± 0.7** |
| PET | Mesothelioma | 26 | — |
| YOU | Mesothelioma | 23 | — |
| PC-3 | Prostate Cancer | 21 | — |
| DU-145 | Prostate Cancer | 23 | — |
| SW-876 | Liposarcoma | 14.57 | — |
| HT-1080 | Fibrosarcoma | 17.16 | — |
| U87 | Glioma | 18 ± 7.1** | 20.5 ± 1.0** |
| LN-18 | Glioma | 9.38 ± 0.79** | 6.64 ± 0.71** |
| T98G | Glioma | 18.2 ± 0.61 | 25.4 ± 0.28** |
| U251 | Glioma | 17 ± 1.2** | — |
| HCT-116 | Colorectal Cancer | 10.5 ± 0.02** | 22.5 ± 5.7** |
| HT-29 | Colorectal Cancer | 5.86 ± 0.2** | 2.75 ± 0.7** |
| HT-29 5m11 | Colorectal Cancer | 10.4 | 21.7 |
| HeLa | Epithelial (Adenocarcinoma) | 15.8 ± 0.3** | 18.2 ± 2.6** |
| HUVEC | Human Umbilical Vein Endothelial Cells | 87 | 47 |
| CHO | Chinese Hamster Ovary | 34.61 ± 0.789*** | 73.7 ± 6.0** |
| HEK | Human Embryonic Kidney | 34.57 ± 0.86** | — |
| 3T3 | Fibroblast | 12.41 ± 0.37** | 11.2 ± 1.1** |
| HaCat | Keratinocyte | 21.2 ± 3.2** | 42.68 ± 8.0** |
| Human Fetus Astrocytes | Astrocytes | 85.55 ± 2.7** | — |

No star = determination,
** = two repetitions,
*** = three repetitions

TABLE 3

| | AAD | AHC # | MW | Formula | IC$_{50}$ µM OVCAR-3 | IC$_{50}$ µM A2780 | IC$_{50}$ µM CHO | IC$_{50}$ µM HUVEC |
|---|---|---|---|---|---|---|---|---|
| 1 | 450 | 0942648 | 382.77 | C18H14ClF3N2O2 | 23.85 ± 1.45 | 33.5 ± 8.5 | 45.87 | 96.5 |
| 2 | 907 | 2000020 | 416.32 | C19H14N2O2F6 | 18.9 ± 4.1 | 27.65 ± 7.15 | 169 | 55.18 |
| 3 | 970 | 2000114 | 432.32 | C19H14N2O3F6 | >100 | >100 | 142 | 139.8 |
| 4 | 1154 | 2001354 | 433.21 | C18H13N2O3F3Cl2 | 20.5 ± 0.5 | 28.0 ± 4.5 | 34.8 | 61.1 |
| 5 | 1336 | 2017686 | 479.20 | C18H12N2O3F5Br | 14.65 ± 1.25 | 17.0 ± 1.2 | 31.8 | 61.3 |
| 6 | 1470 | 2033757 | 468.30 | C19H12N2O3F8 | 12.9 ± 0.3 | 19.5 ± 4.1 | 32.2 | 74.0 |
| 7 | 004 | 2060021 | 416.75 | C18H13N2O3F4Cl | 18.58 ± 2.4 | 27.3 ± 0.5 | 57.3 | 93.0 |
| 8 | 2009 | 2062412 | 416.75 | C18H13N2O3F4Cl | 34.3 ± 4.3 | 75.9 ± 1.9 | 198 | 129.9 |
| MPL-(S) | 1566 | 2082782 | 473.39 | C20H13N3O2F6S | 7.9 ± 0.9 | 11.3 ± 0.9 | 34.61 | 65.0 |
| MPL-(R) | 2224 | 2102224 | 473.39 | C20H13N3O2F6S | 8.0 ± 0.7 | 14.75 ± 0.45 | 23.4 | 108.8 |

OVCAR-3, A2780 are human epithelial ovarian cancer; CHO = Chinese hamster ovarian cells; HUVEC = human umbilical vein endothelial cells

TABLE 4

Amino-acetonitrile derivatives (AADs) according to Table 3

| AAD | | R1 | R2 | R3 | R4 |
|---|---|---|---|---|---|
| 1566 | (MPL) | CN | H | CF$_3$ | SCF$_3$ |
| 2105 | (MPL-SO) | CN | H | CF$_3$ | SOCF$_3$ |
| 4670 | (MPL-SO$_2$) | CN | H | CF$_3$ | SO$_2$CF$_3$ |
| 450 | | H | H | Cl | CF$_3$ |
| 907 | | H | H | CF$_3$ | CF$_3$ |
| 970 | | H | H | CF$_3$ | OCF$_3$ |
| 1154 | | Cl | H | Cl | OCF$_3$ |
| 004 | | F | H | Cl | OCF$_3$ |
| 2009 | | H | F | Cl | OCF$_3$ |
| 1336 | | F | F | Br | OCF$_3$ |
| 1470 | | F | F | CF$_3$ | OCF$_3$ |

According to Table 3, "MPL-(R)" refers to N-[(1R)-1-cyano-2-(5-cyano-2-trifluoromethyl-phenoxy)-1-methyl-ethyl]-4-trifluoromethylsulfanyl-benzamide, and "MPL-(S)" refers to N-[(1S)-1-cyano-2-(5-cyano-2-trifluoromethyl-phenoxy)-1-methyl-ethyl]-4-trifluoromethylsulfanyl-benzamide.

According to the results shown in Table 3, the ratio of IC50 values (normal cell/cancer cell) for AADs 907, 1336, 1470 and 2224 (MPL-(R)) show particularly high activity. Further, AADs 2224 (MPL-(R)) and AAD 1566 (MPL-(S)) were found to be equipotent. It is noted that the (R)-enantiomer MPL-(R) has previously been shown to have no anthelmintic activity.

Figure 8:
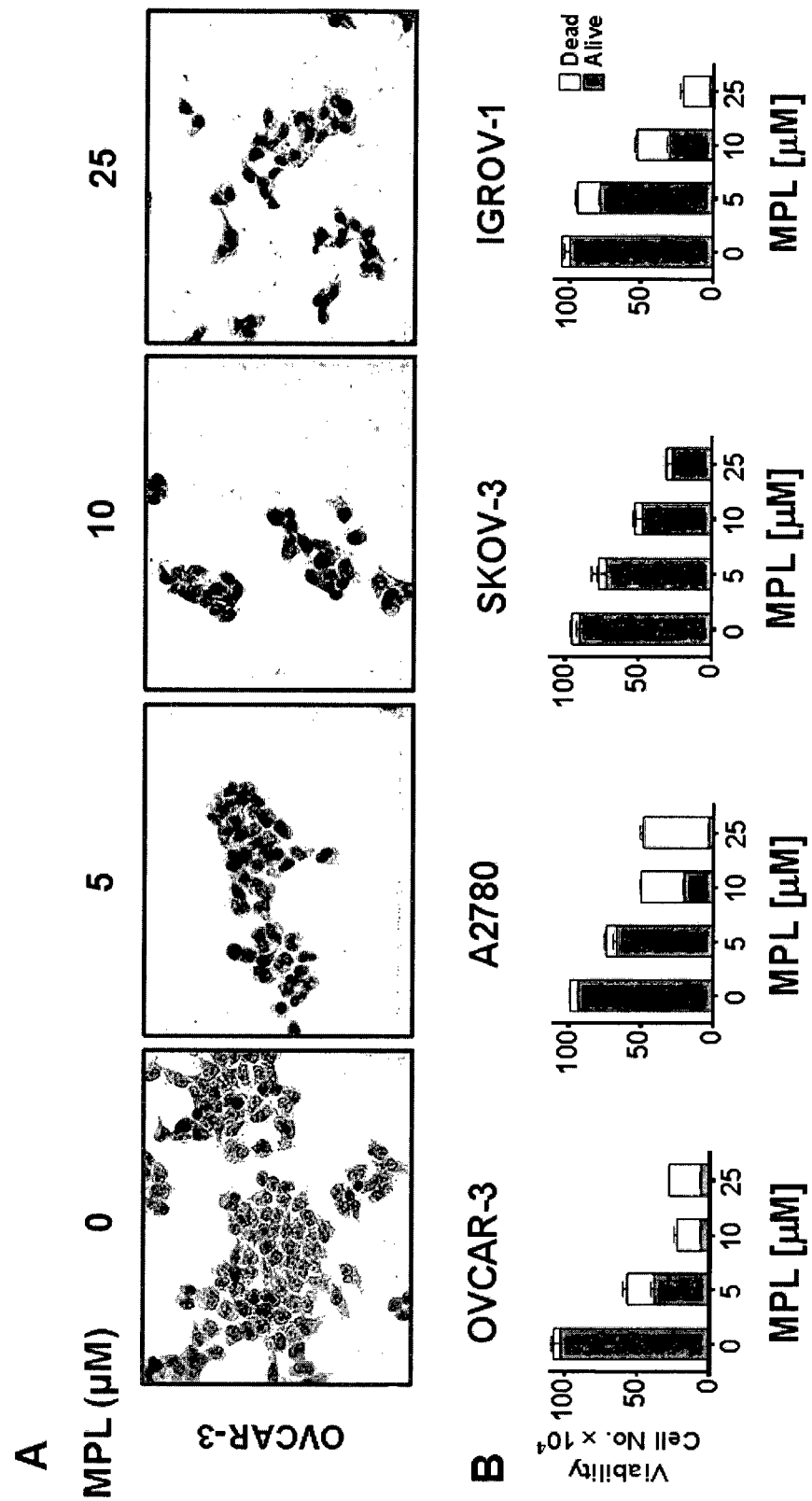
FIG. 8 shows MPL interference with cell viability. A) Microscopic image of OVCAR-3 cells exposed to MPL (0, 5, 10, 25 μM) for 72 h. Human ovarian cancer cell lines OVCAR-3, A2780, SKOV-3, IGROV-1 were cultured in the presence of MPL (0, 5, 10, 25, μmol/L) for 72 h. Effect of MPL on cell viability was assessed using the standard Trypan blue assay. Control (vehicle treated) cells were taken to present 100% viable and the MPL treated groups are expressed as percentage of control. Each drug concentration was tested in quadruplicate and each experiment was repeated at least twice. The data (mean±SEM) are presented as % control. For statistical comparisons, each drug treated group was compared with the control group using Student's t test and a p value of 0.5 or less was considered to present a significant change (p<0.5), *=<0.05, <0.01, *=p<0.001.
Figure 9:
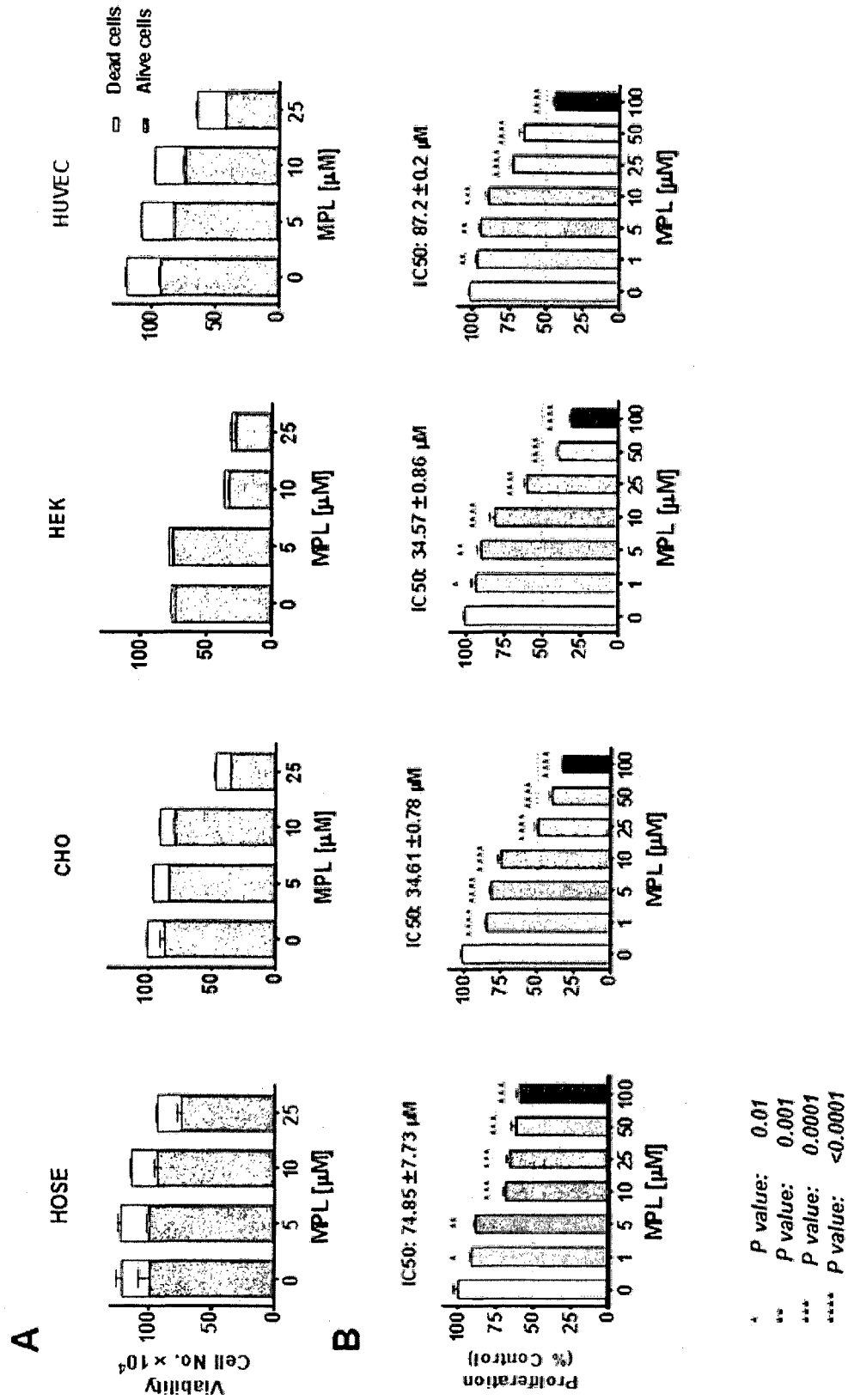
FIG. 9 shows the effect of MPL on the viability of normal cells and shows the anti-proliferative effect of MPL is cancer cell orientated. Normal cells HOSE, CHO, HEK and HUVEC were cultured in the presence of MPL (0, 5, 10, 25 μmol/L) for 72 h. Effect of MPL on cell viability was assessed using the standard Trypan blue assay. Results are presented as mean±SEM compared to control (100%).
Figure 10:
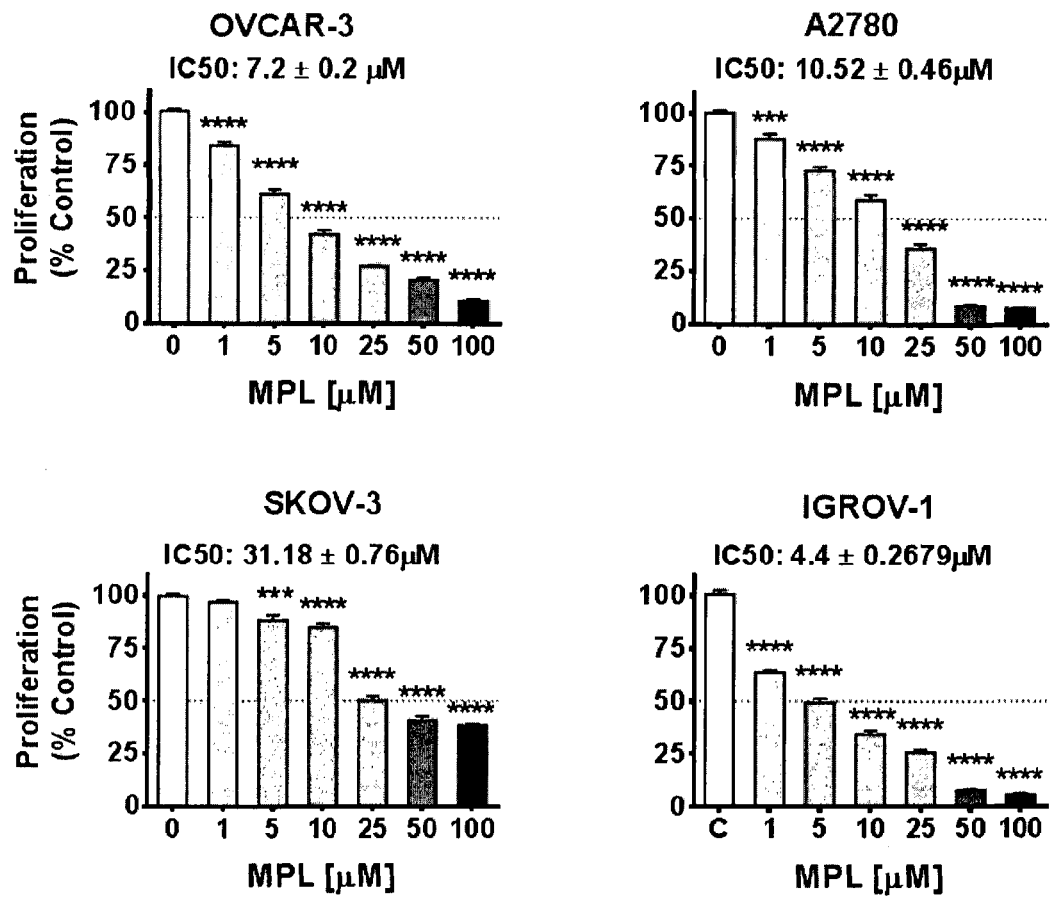
FIG. 10 shows how MPL inhibits cell proliferation. Human ovarian cancer cell lines OVCAR-3, A2780 and SKOV-3 and IGROV-1 were all cultured in the presence of MPL (0, 5, 10, 25, 50 and 100 μmol/L) for 72 h. Effect of MPL on cell proliferation was assessed using the SRB assay. Control (vehicle treated) cells were taken to present 100% proliferation and the MPL treated groups are expressed as percentage of control. Each drug concentration was tested in quadruplicate and each experiment was repeated at least twice. The data (mean±SEM) are presented as % control. For statistical comparisons, each drug treated group was compared with the control group using Student's t test. (A): Atropine: muscarinic Ach. receptor antagonist, Tobucorarine: nicortinic Ach. receptor antagonist, Mecamylamine: nonselective, noncompetitive nicotinic receptor antagonist; (B): Carbachol: muscarinic nicotinic ach. receptor agonist, Nicotine: Nicotinic ach. receptor agonist, Alpha-bungarotoxin: selective α7, nicotinic ach receptor agonist.

In brief, MPL and MPL-SO2 were tested in vitro against a wide range of cancer cell-lines with extensively different disease characteristics. For further detailed studies, human ovarian cancer cell lines OVCAR-3 and A2780 were chosen. Additionally, normal human ovarian surface epithelial cells (HOSE) and were cultured in the presence of MPL (0, 5, 10, 25, 50 and 100 µM) for 72 h. Cell viability was assessed using Trypan blue assay (FIG. 8). Similarly, effect of MPL on the growth of normal epithelial, endothelial, embryonic and fetal cells were investigated (FIG. 9) while cell proliferation was assessed using the SRB assay (FIG. 10). Control (vehicle treated) cells were taken to present 100% proliferation and the MPL treated groups are expressed as percentage of control±SEM. Each drug concentration was tested in quadruplicate and each experiment was repeated at least twice. For statistical comparisons, each drug treated group is compared to the control group using Student's t test. To examine concentration dependent drug effect, analysis of variance (ANOVA) was used. P values are: *=<0.05; <0.01 and *=<0.001, **** p<0.0001. Results presented in Table 2 reveal that MPL exerts high antiproliferative activity in cancer cell lines, whereas, normal cells are far less affected. In

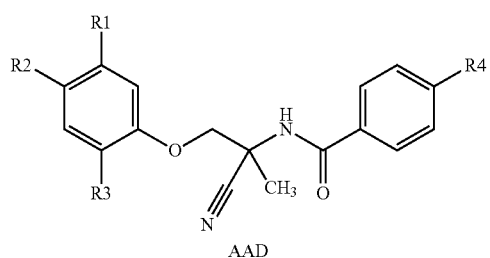

Figure 11:
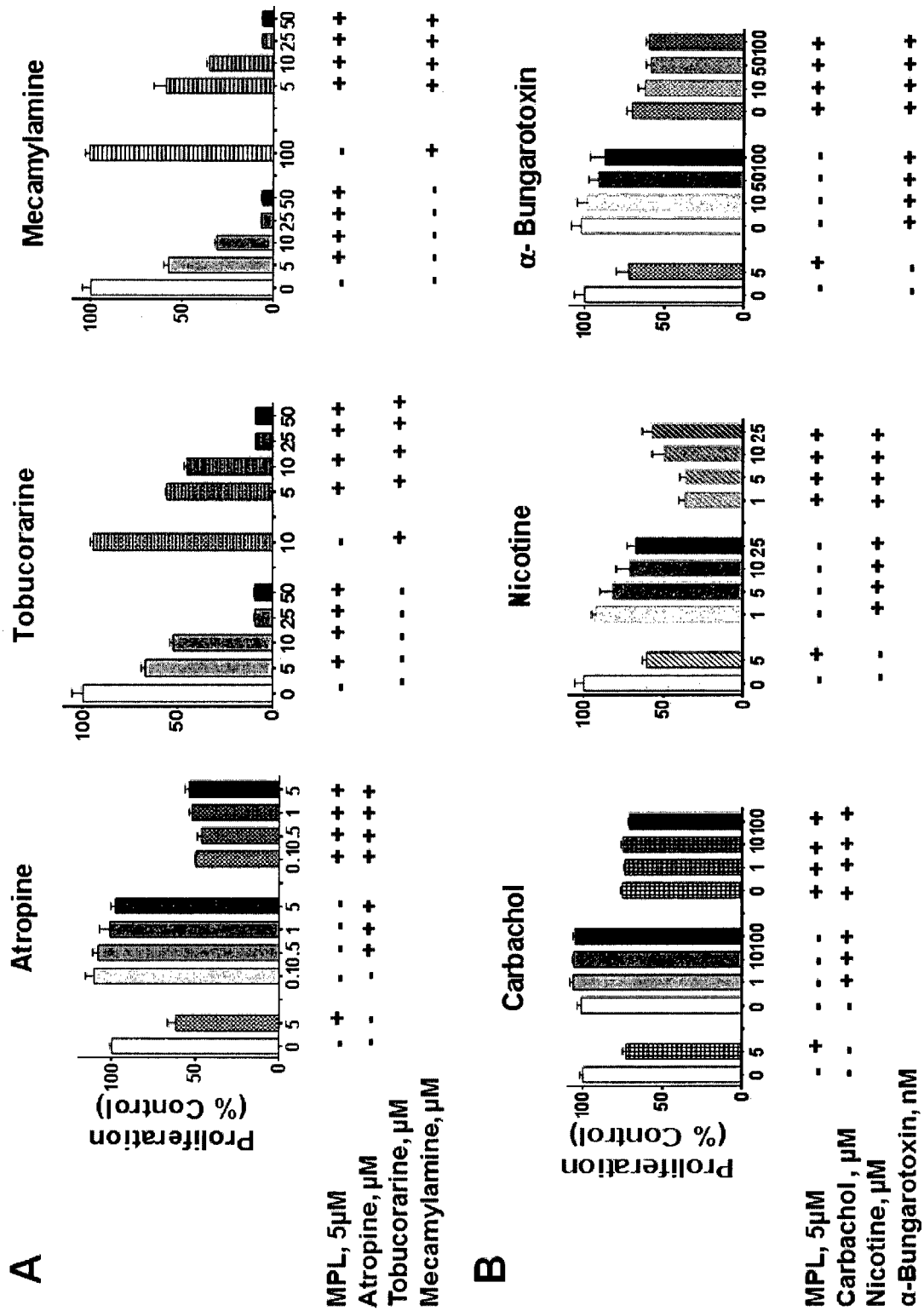
FIG. 11 shows that the MPL antiproliferative effect is independent of nicotinic receptors. Cells were pre-treated (30 min) with increasing concentrations of nicotine, carbachol or the receptor antagonists, atropine, mecamylamine, tubocurarine, and α-bungarotoxin. MPL (5 μM) was added and left in the cell culture incubator for 72 h. Each drug concentration was tested in quadruplicate and each experiment was repeated twice. Combine values (mean±SEM) are presented as % control.
Figure 12:
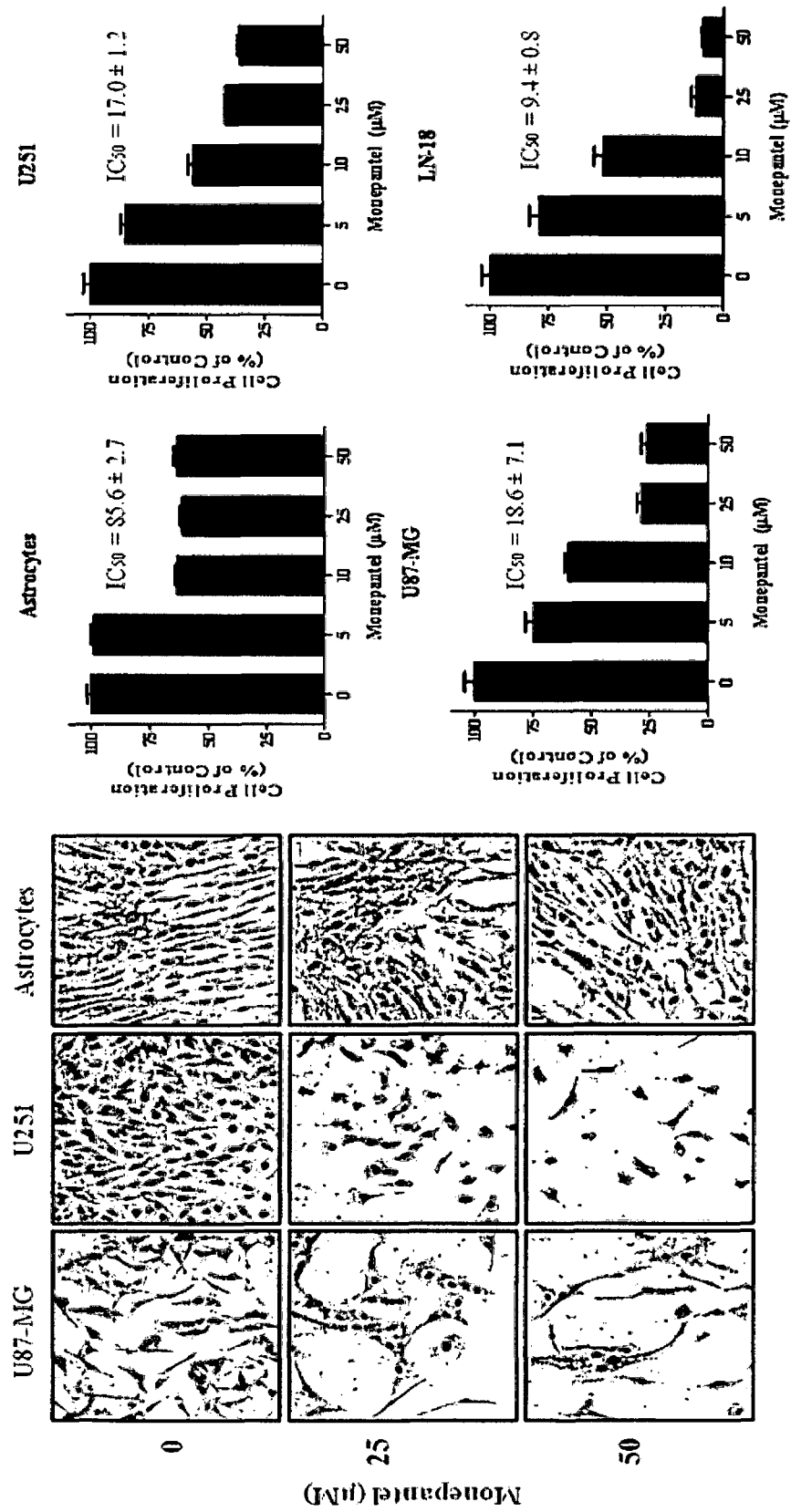
FIG. 12 shows how MPL inhibits proliferation of glioma cells. Comparison of the effect of MPL treatment (0, 5, 10, 25, 50 μM; 72 h) on the proliferation of U87-MG, U251 glioma cell lines versus normal astrocytes under normal cell culture conditions and using SRB proliferation assay. Data are presented as % control.
Figure 13:
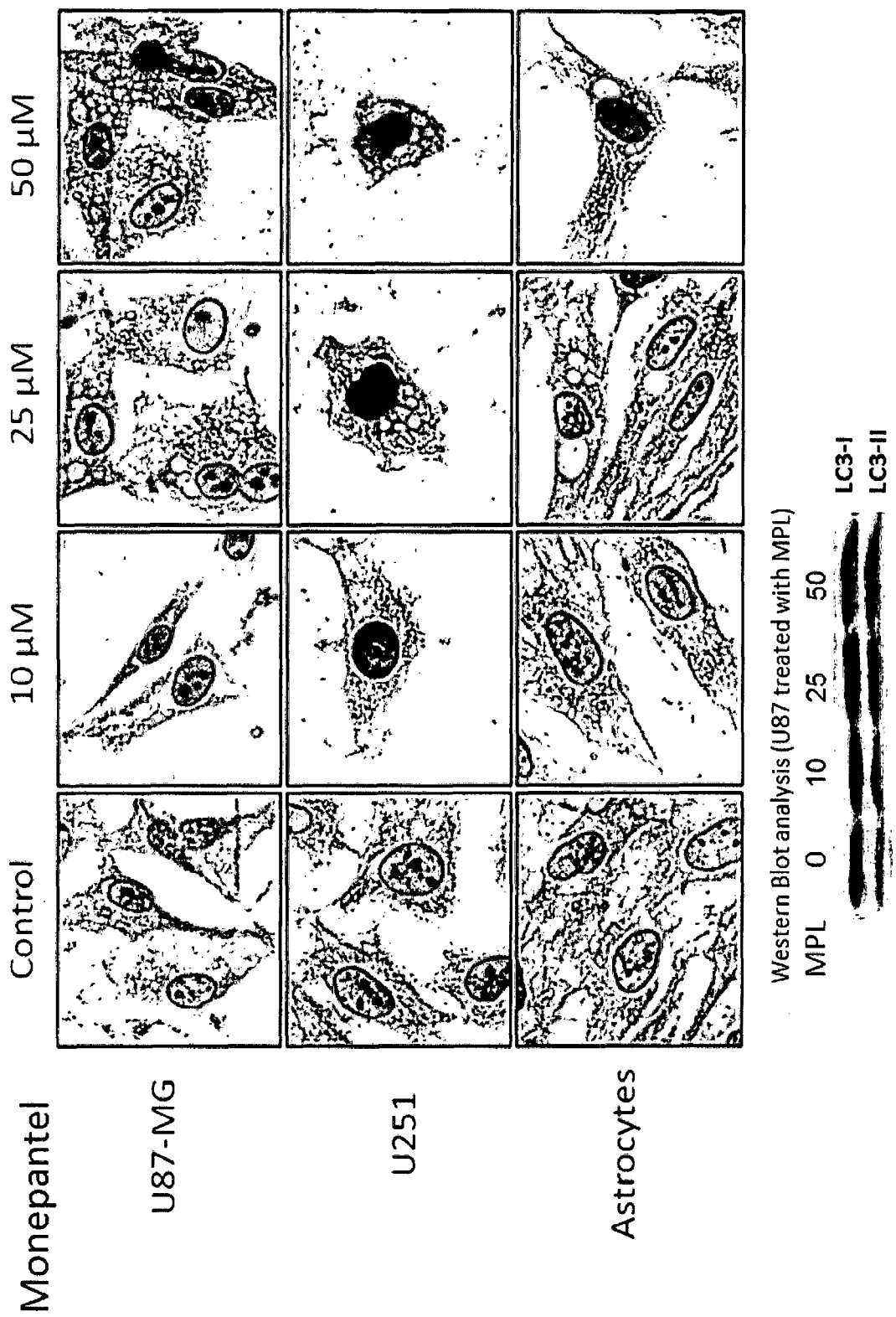
FIG. 13 shows how MPL induces autophagy. The treatment of chemo-resistant U87 glioma cells with MPL leads to autophagy, which is confirmed by increased expression of LC3-II in a concentration-dependent manner. U87-MG and U251 glioma cells treated with MPL demonstrated concentration-dependent formation of autophagy (shown as vacuoles). Concentration-dependent conversion of LC3-I to LC3-II confirms the increasing phenomenon of autophagy in these cells.

AAD order to find out if the MPL effect is mediated through the nicotinic acetyl choline receptor and in particular the nACHR7 subtype, cells were pretreated with antagonists and then exposed to MPL (FIG. 11).

Results obtained for MPL-SO2 are also presented. It can be seen that MPL-SO2 acts in a similar order as the parent drug MPL. The range of $IC_{50}$ values are very close and suggest that MPL-SO2 is as effective as MPL in suppressing cancer cell proliferation (Table 2).

MPL Inhibits Colony Formation

Figure 1:
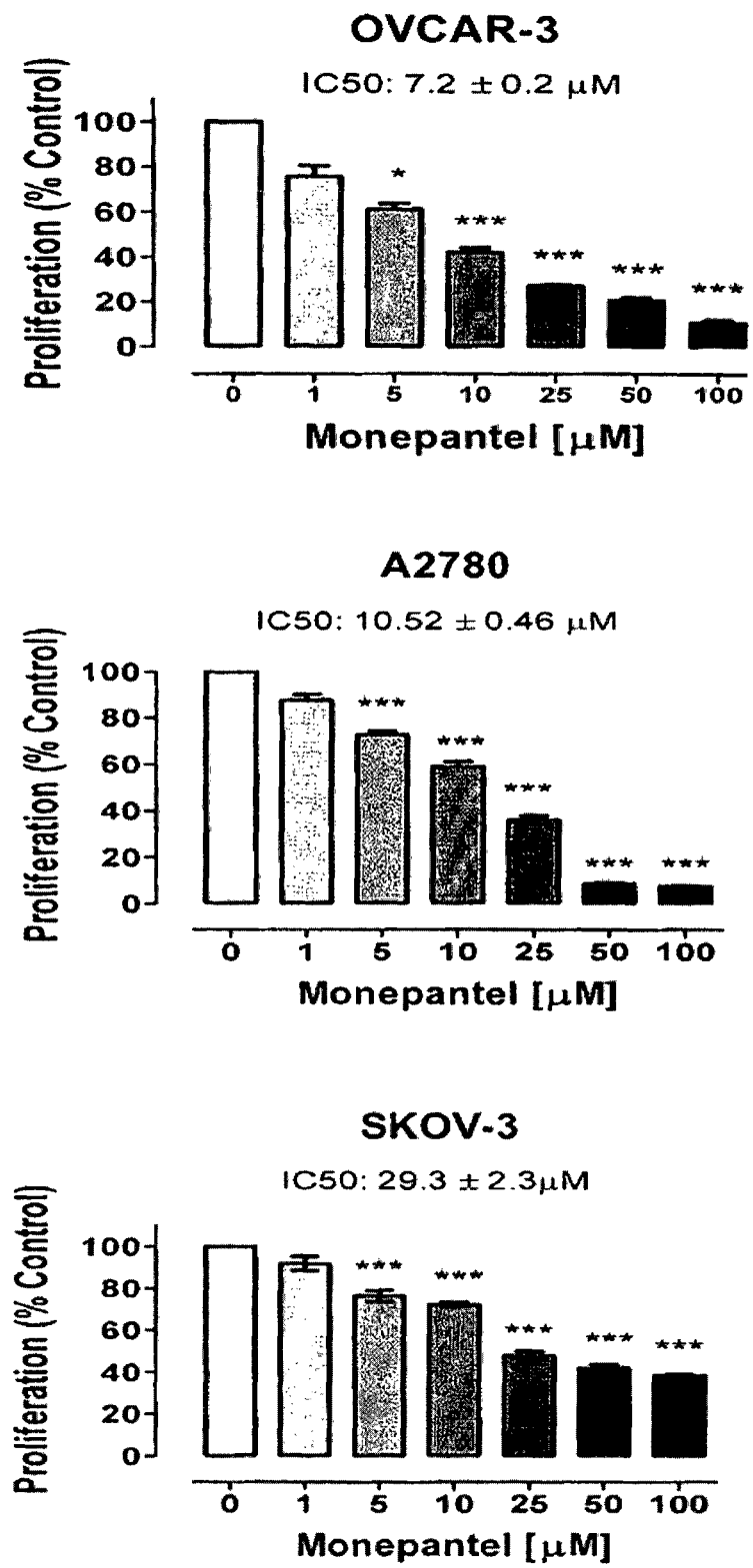
FIG. 1 shows the inhibition of cell proliferation by MPL. Ovarian cancer cell lines OVCAR-3, A2780 and SKOV-3 and normal HUVEC (control) were all cultured in the presence of MPL (0, 1, 5, 10, 25, 50 and 100 µmol/L) for 72 hours. The effect of MPL on cell proliferation was assessed using the SRB assay. Control (vehicle treated) cells were taken to present 100% proliferation and the MPL treated groups are expressed as percentage of control. Each drug concentration was tested in quadruplicate and each experiment was repeated at least twice. The data (mean±SEM) are presented as a percentage of the control. For statistical comparisons, each drug treated group was compared with the control group using Student's t test.
Figure 2:
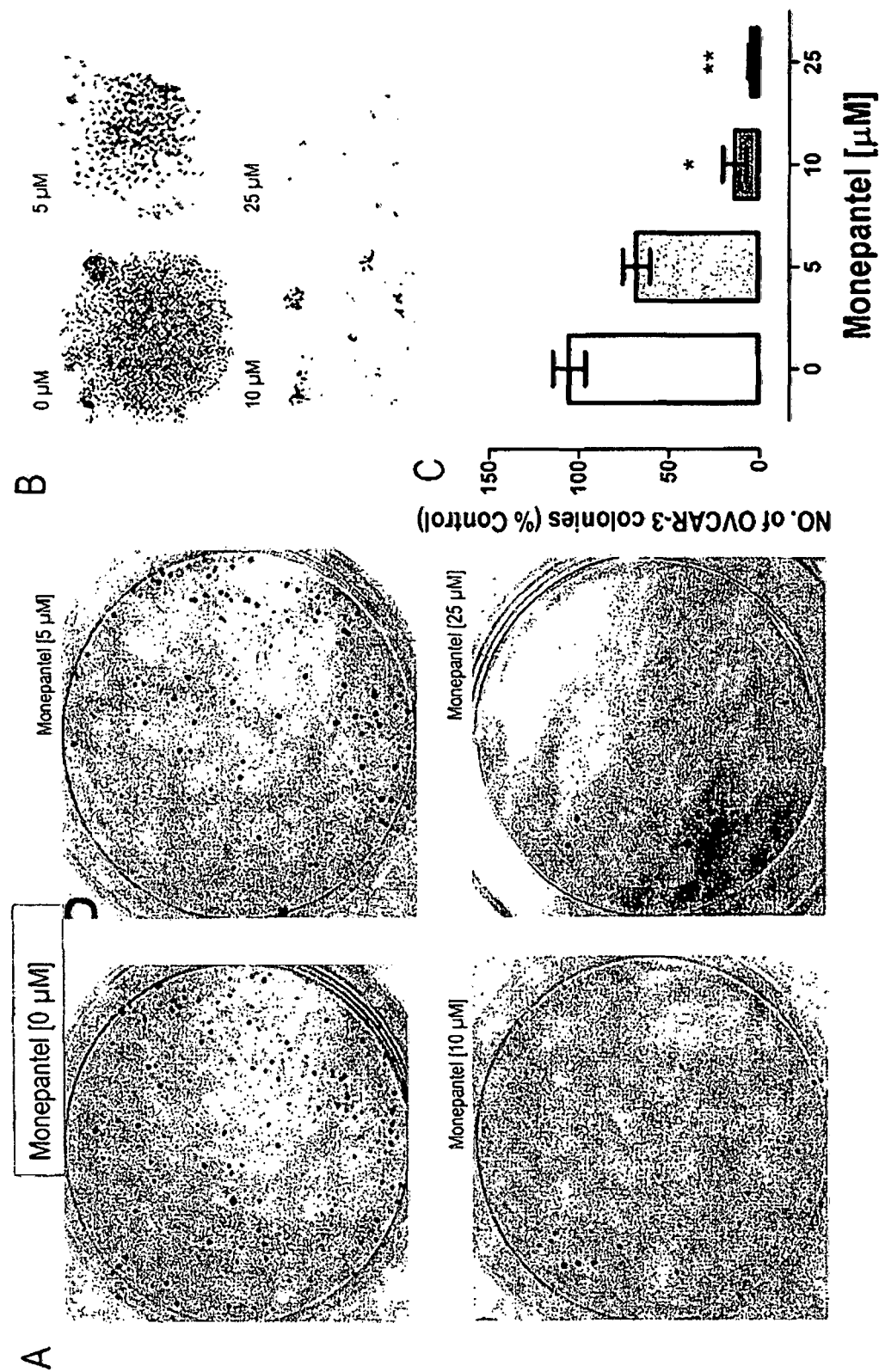
FIG. 2 shows the effect of MPL on the colony formation activity of OVCAR-3 cells. Following incubation of cells with MPL (0, 5, 10 and 25 µmol/L) for 72 hours, cells were washed, transferred to agar plates, cultured with their regular growth medium and incubated under standard conditions for 2 weeks. Cells were then fixed with 100% methanol and stained with 1% crystal violet. Colonies (a cluster of cells greater than 50) were counted under a microscope (magnification ×5). The number of colonies counted for different experimental groups is expressed as a percentage of the control.

To investigate whether MPL also hinders the reproductive integrity and the ability of cell lines to establish colonies, the clonogenic activity of cells exposed to MPL was investigated. Following 72 h exposure to various concentrations of MPL, cells were washed and then incubated in drug free media for 2 weeks. It was found that MPL profoundly hinders colony formation by these cells. Higher concentrations of MPL led to almost complete loss of clonogenic ability (FIG. 2).

Figure 14:
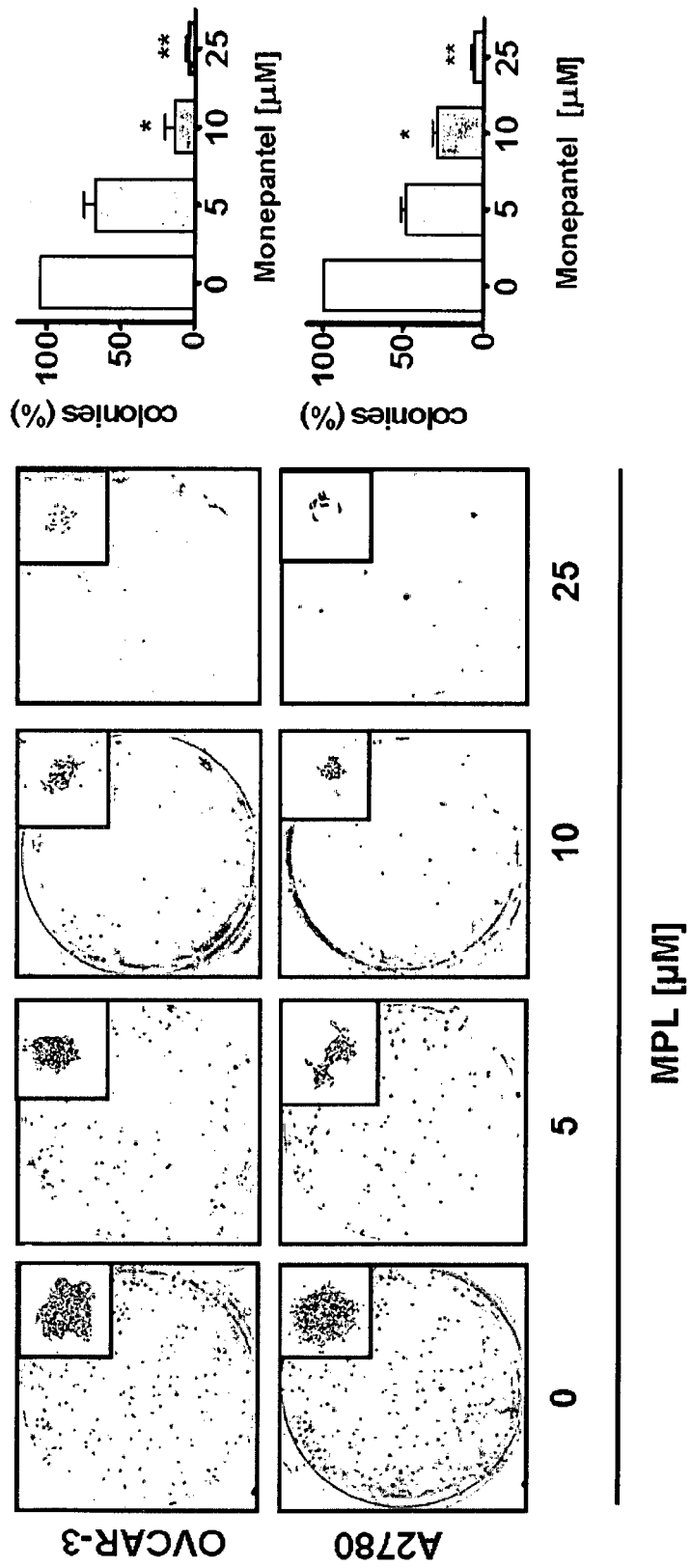
FIG. 14 shows the effect of MPL on the colony formation activity of OVCAR-3 and A2780 cells. Following incubation of cells with MPL (0, 5, 10, 25 μM) for 72 h, cells were washed and then transferred to agar plates, cultured with their regular growth medium and incubated under standard conditions for 2 weeks. Cells were then fixed with 100% methanol and stained with 1% crystal violet. Colonies (cluster of cells greater than 50) were counted under microscope (magnification ×5). Number of colonies counted for different experimental groups is expressed as % of control.
Figure 15:
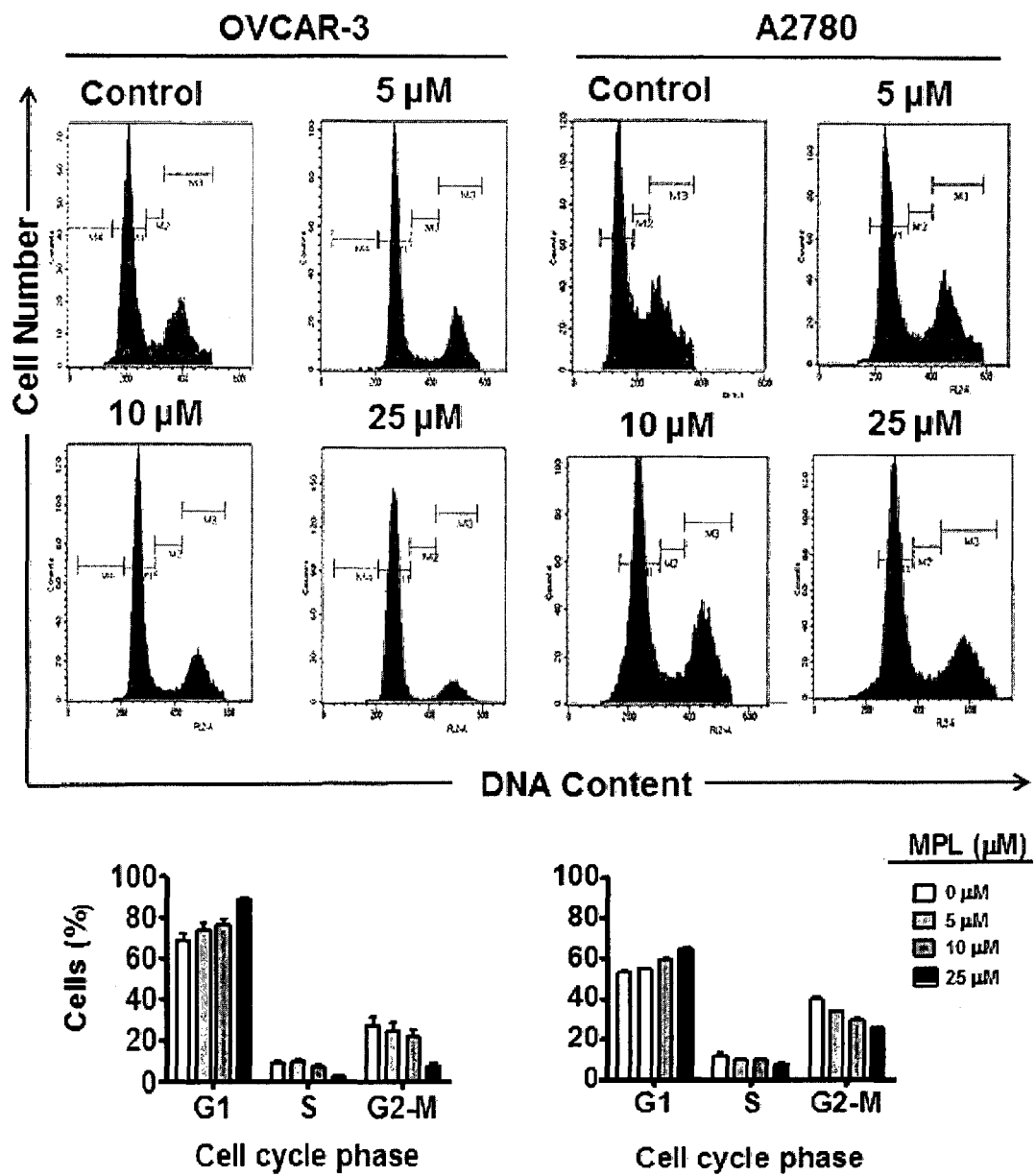
FIG. 15 shows how MPL interferes with the cell cycle progression of ovarian cancer cell lines. OVCAR-3 or A2780 cells were treated with MPL (0, 5, 10, 25 μM) for 48 h and examined by flow cytometric analysis (FACS) after staining the cells with PI. The Figure and data present MPL-induced change in cell distribution in various phases of the cell cycle, here shown as percentage of cells in G1, S and G2/M phases. Each value represents mean±SEM of 2 independent determinations.

To determine the effect of MPL on cell integrity and capacity to rid itself from drug effects following drug exposure and withdrawal, cells were incubated with MPL (0, 5, 10, 25 µM) for 72 h, washed with PBS, transferred to agar plates, cultured with growth medium and incubated under standard conditions for 2 weeks. Cells were then fixed with 100% methanol and stained with 1% crystal violet. Colonies (Cluster of cells greater than 50) were counted under microscope (magnification ×5). Number of colonies counted for different experimental groups is expressed as percentage of the control (FIG. 14). These results demonstrate concentration-dependent inhibition of colony formation by MPL.

Figure 3A:
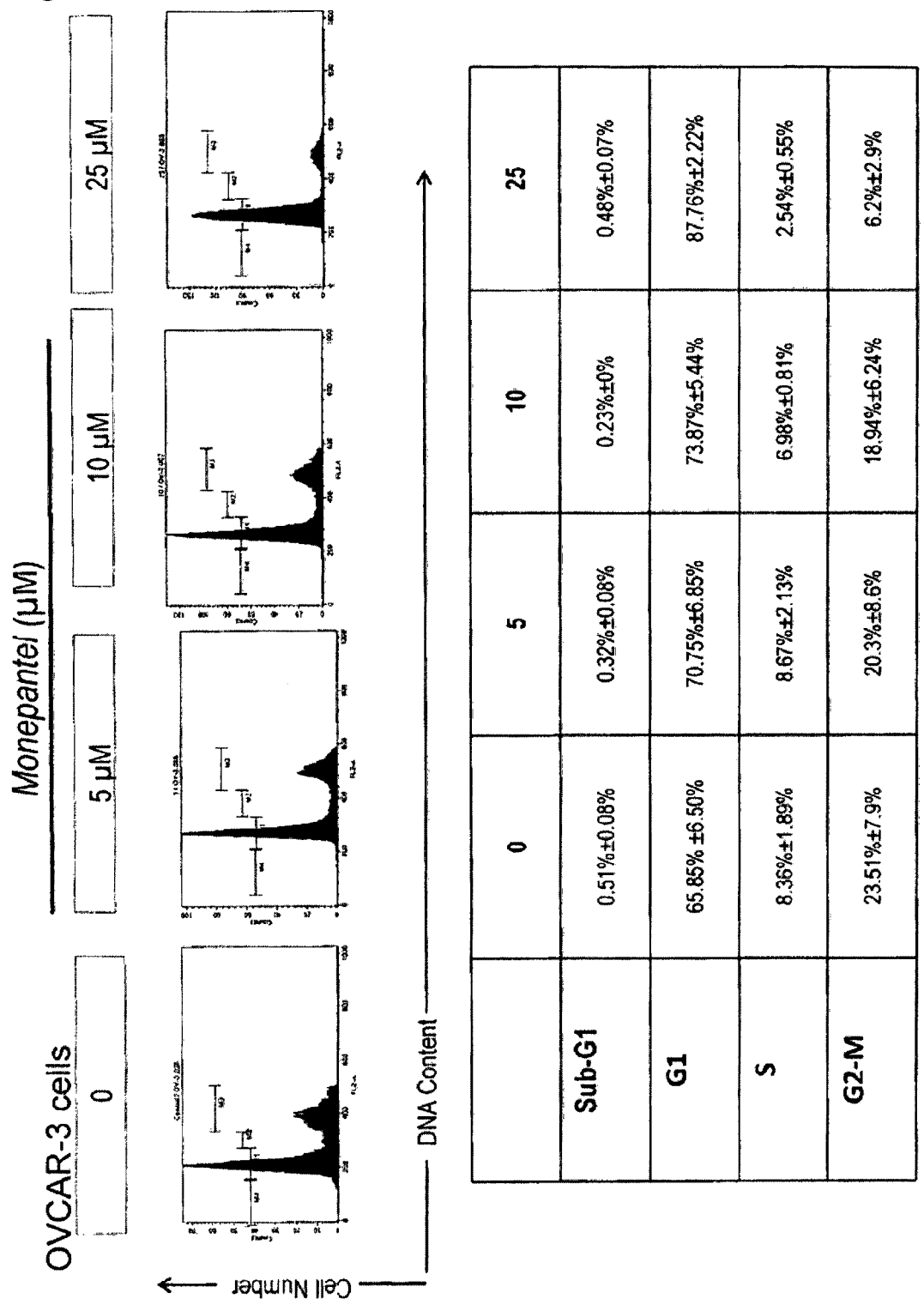
FIG. 3 shows how MPL interferes with the cell cycle distribution of ovarian cancer cell lines. OVCAR-3 (FIG. 3a) or A2780 (FIG. 3b) cells were treated with MPL (0, 5, 10 and 25 μmol/L) for 48 hours. Propodium iodide stained cells were analysed for DNA content using flow cytometric analysis. The results (see table) are shown as a percentage of cells in G1, S and G2/M phases. Each value represents mean ±SEM of 2 independent experiments.
Figure 3B:
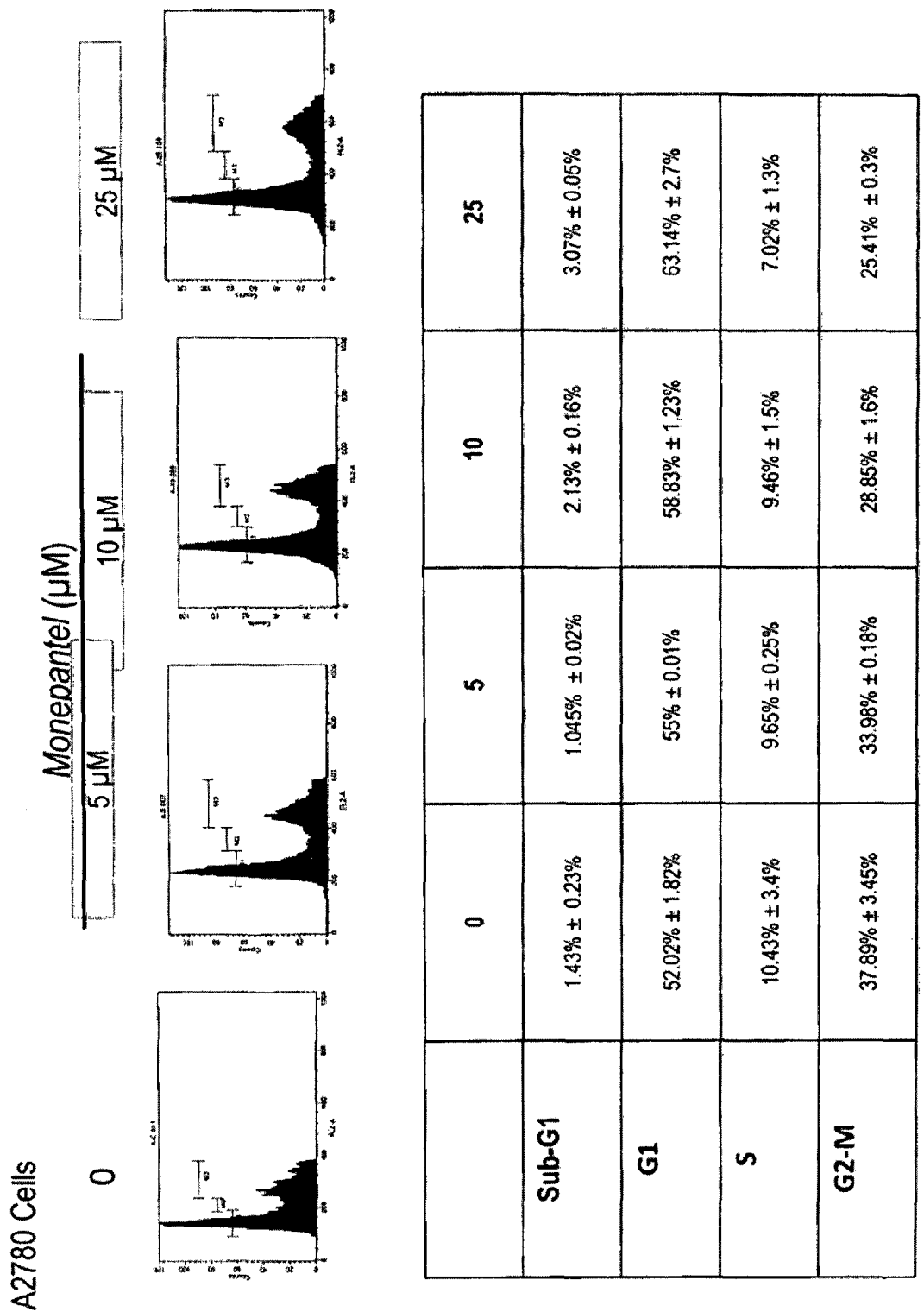
Figure 4:
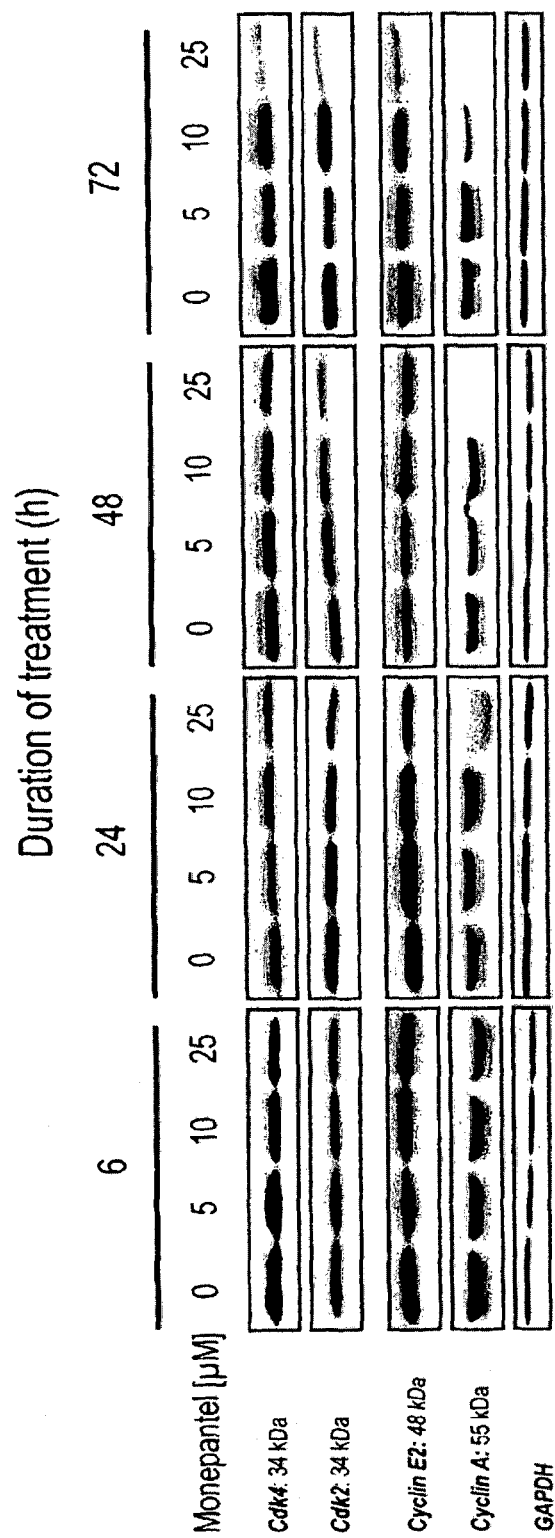
FIG. 4 shows how MPL interferes with the expression of cell cycle regulatory proteins cdk2, cdk4 and cyclins E and A. Cells were treated with MPL (0, 5, 10 and 25 μmol/L) for 48 hours. Whole-protein extracts were obtained and separated by electrophoresis and immunoblots were probed with the indicated antibodies. Western blot analysis showing the levels of these proteins in each extract was analysed using the relevant antibodies. The image represents the exposed radiographic film scanned. The house-keeping gene (GAPDH) was used to confirm similar protein loading and blot transfer.

MPL Arrests Cell Cycle Through Down Regulating the Expression of Cyclines and Cycline -dependent Kinases To investigate the mechanism(s) through which MPL inhibits cell proliferation and colony formation, the effect of the MPL on the cell cycle by means of flow cytometry was examined. It was found that MPL interferes with the cell cycle progression (FIG. 3). Progression of cells exposed to MPL was arrested in the G1 phase in a concentration and time-dependent manner. Accumulation of cells in the G1 phase was accompanied by sharp decline of percentage of cells in the S and G2-M phases. To study the molecular mechanisms involved in the MPL-induced cell cycle arrest, the expression of cell cycle regulatory proteins cdk2, cdk4, cyclins A, and E was examined. MPL treated cells expressed lower levels of cdk2, cdk4, cyclins A, and E (FIG. 4).

MPL Arrests Cell Cycle Through Down Regulating the Expression of Cyclines and Cycline -dependent Kinases Leading to Induction of PARP-1 Cleavage.

Figure 16:
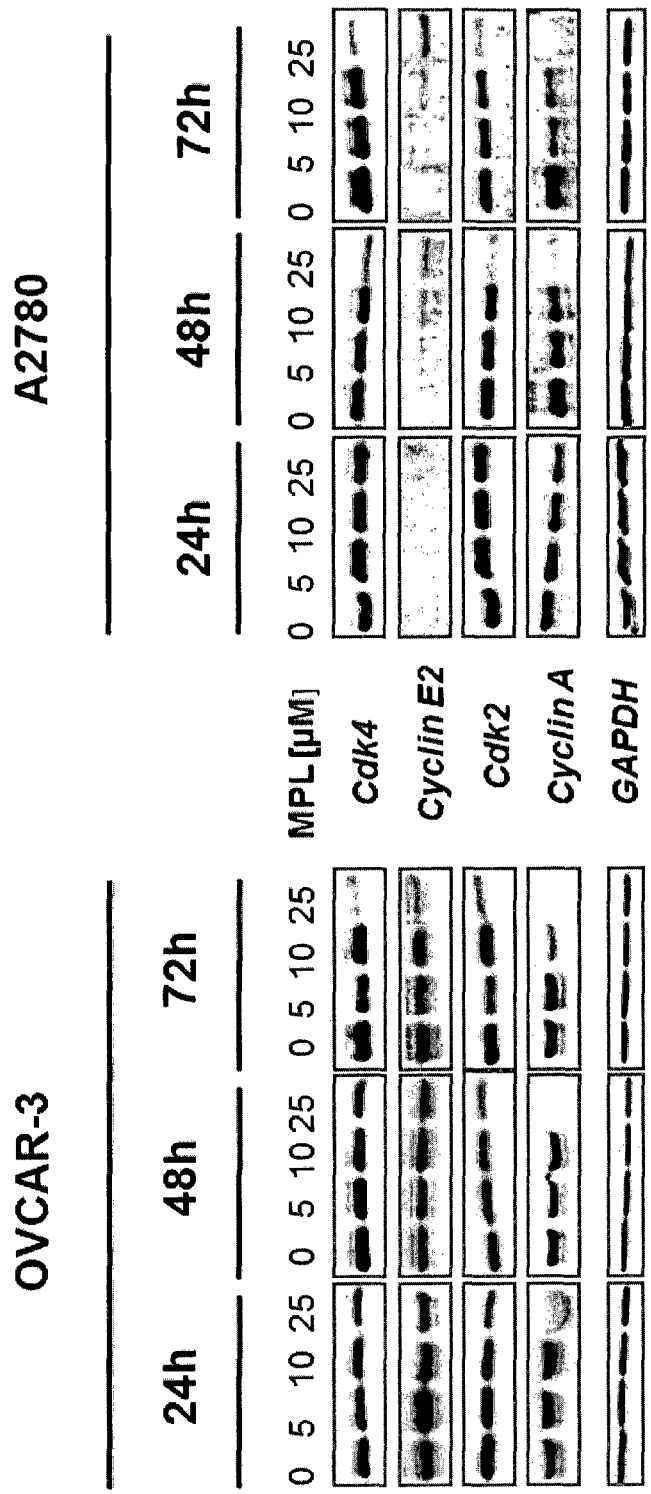
FIG. 16 shows how MPL interferes with the expression of cell cycle regulatory proteins cdk2, cdk4, cyclines E and A. Cells were treated with MPL (0, 5, 10, 25 μM) for 24, 48 h or 72 h. Whole-protein extracts were obtained and separated by electrophoresis, and immunoblots were probed with the indicated antibodies. Western blot analysis showing the levels of these proteins in each extract was analysed using the relevant antibodies. The image represents the exposed radiographic film scanned. The house-keeping gene (GAPDH) was used to confirm similar protein loading and blot transfer.

To find out the mechanism(s) through which MPL inhibits cell proliferation and colony formation, the effect of MPL on the cell cycle was examined by means of flow cytometry (FACS). It was found that MPL interferes with the cell cycle progression (FIG. 22). In cells exposed to MPL cell cycle was arrested in the G1 phase in a concentration and time-dependent manner. Accumulation of cells in the G1 phase was accompanied by sharp decline in percentage of cells in the S and G2-M phases. To study the molecular mechanisms involved in the MPL-induced cell cycle arrest, the expression of cell cycle regulatory proteins cdk2, cdk4, cyclins A, and E was examined. MPL treated cells expressed lower levels of cdk2, cdk4, cyclin E, and cyclin A (FIGS. 4 and 16).

MPL Induces PARP-1 Cleavage

Figure 5:
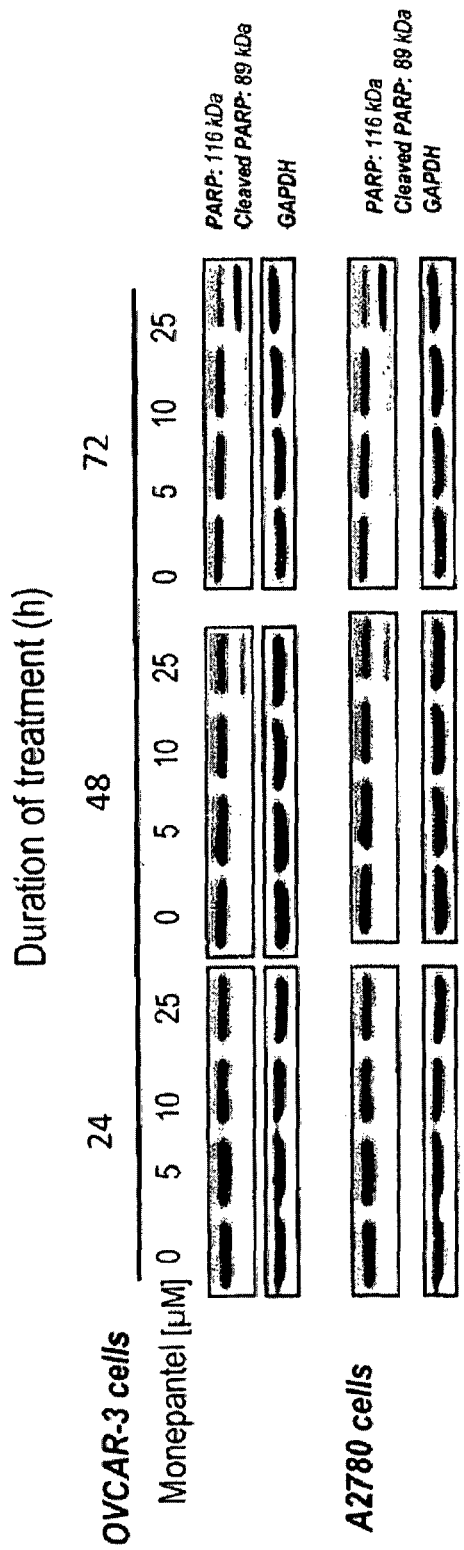
FIG. 5 shows an immunoblot analysis of PARP and cleaved PARP in MPL treated cells. OVCAR-3 and A2780 cells grown under cell culture conditions were incubated with various concentrations of MPL [0, 5, 10, 25 μM] for 24, 48 or 72 hours. Cell lysates were then prepared and analysed by western blotting for the determination of PARP and cleaved PARP.

To investigate whether the MPL-induced cell death involves cleavage of PARP, western blot analysis of lysates of MPL-treated cells for PARP-1 and cleaved PARP-1 was carried out. Cleavage of PARP-1 promotes apoptosis by preventing DNA-repair-induced survival. PARP helps cells to maintain their viability and hence cleavage of PARP facilitates cellular disassembly and serves as marker of cells undergoing apoptosis. FIG. 5 shows that PARP was cleaved in MPL treated cells.

MPL Induces PARP Cleavage

Figure 17:
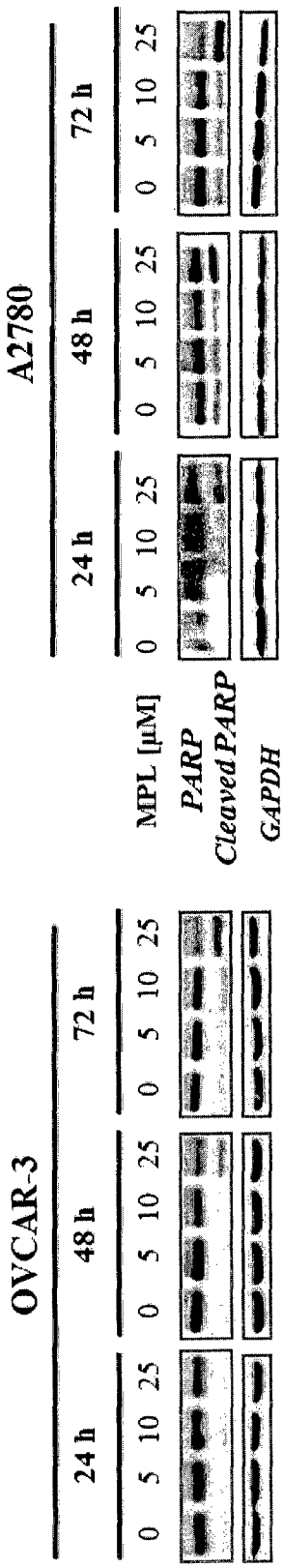
FIG. 17 shows how MPL cleaves PARP. Exposure of OVCAR-3 or A2780 cells to MPL (0, 5, 10, 25 μM) for 24, 48 or 72 h causes cleavage of PARP, which leads to cellular disassembly and serves as a marker of dying cells.

Western blot analysis of cell lysates prepared from MPL treated OVCAR-3 and A2780 cells showing highly induced cleavage of PARP representing cell death (FIG. 17).

MPL Reduces Cellular ATP Levels

Figure 18A:
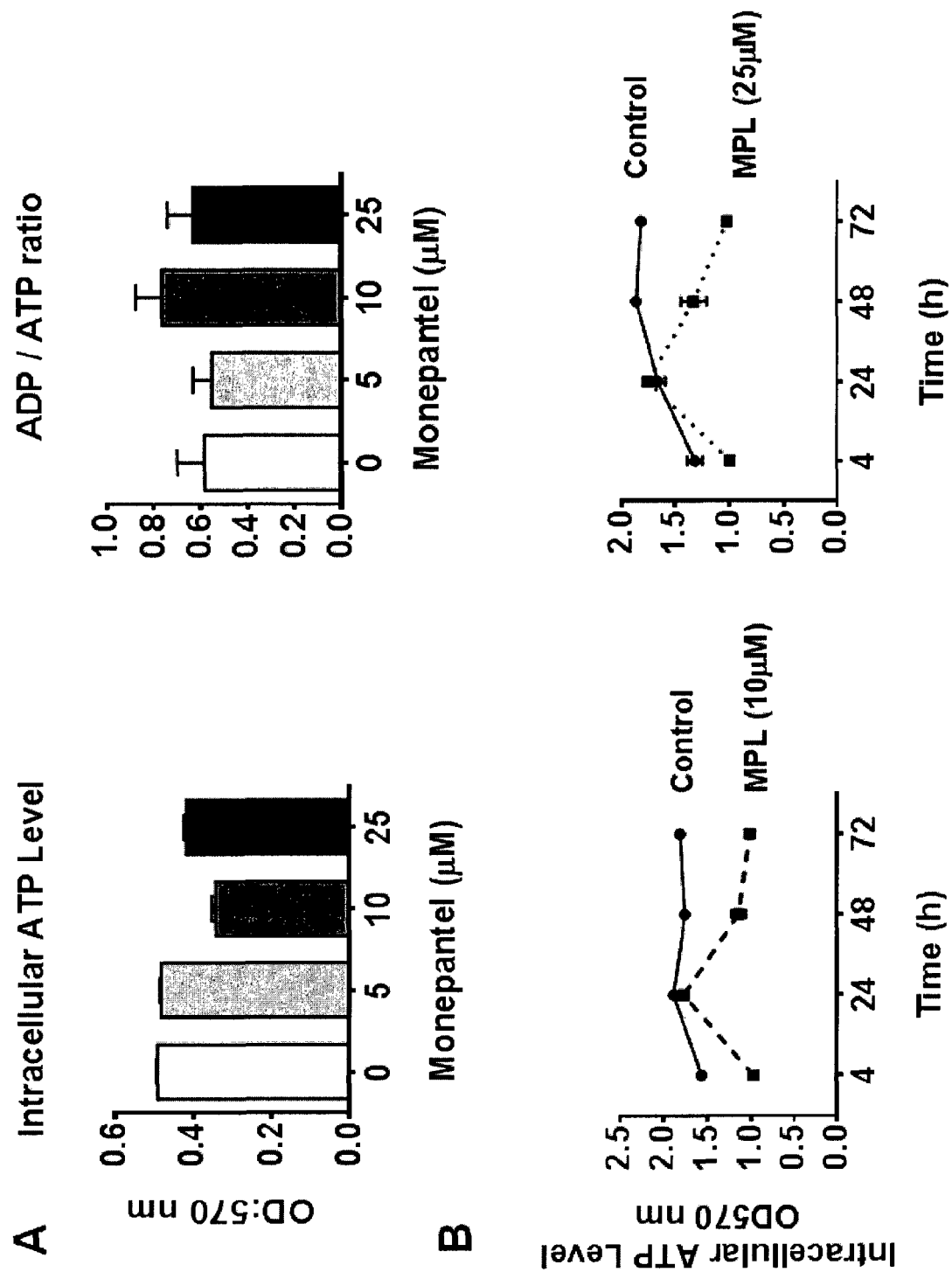
FIGS. 18A and 18B show how MPL decreases ATP levels. Exposure of OVCAR-3 or A2780 cells to MPL (0, 5, 10, 25
Figure 18B:
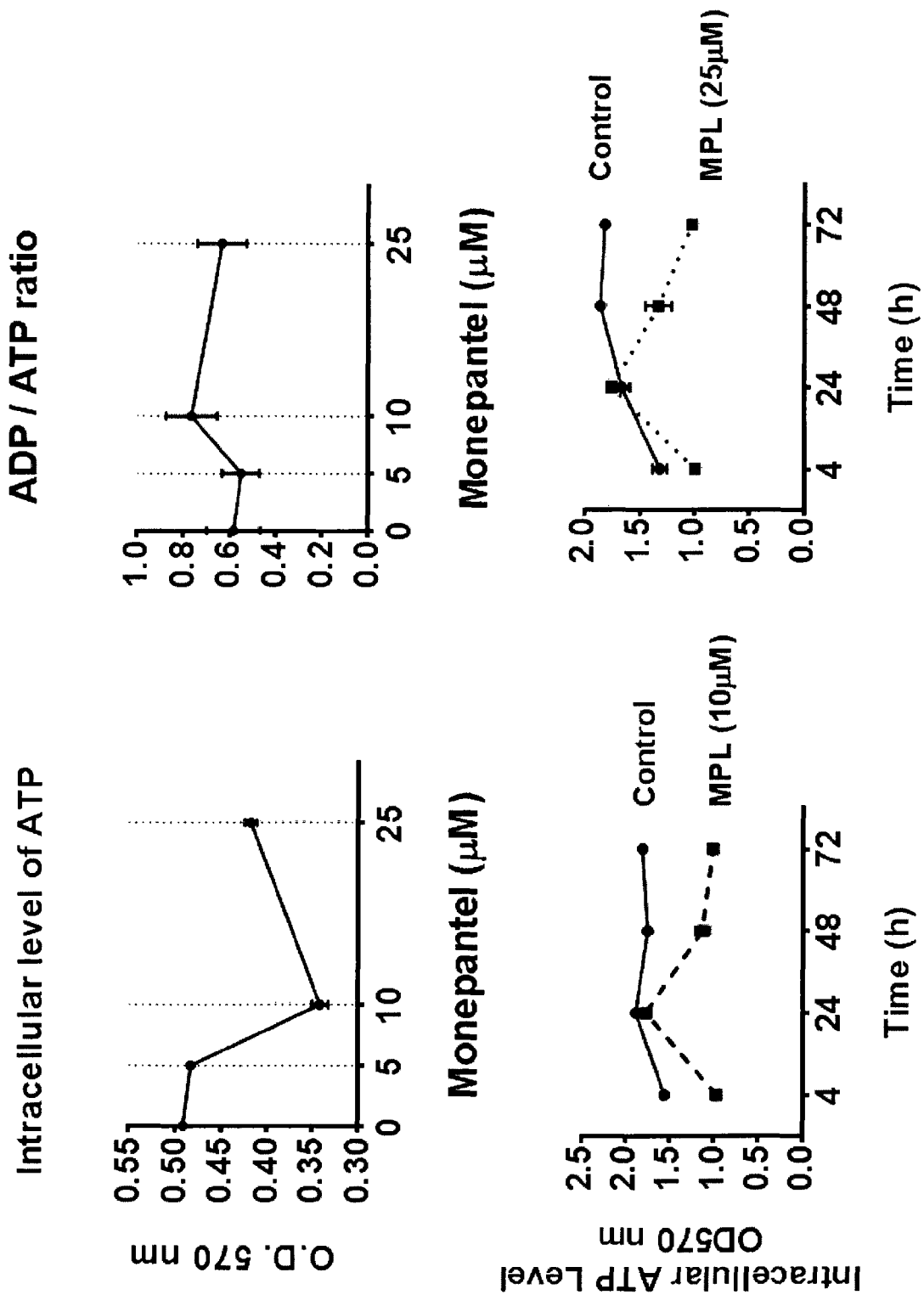

As depicted in FIGS. 18A and 18B, treatment of OVCAR-3 or A2780 cells with MPL causes a reduction in ATP levels found in the cell.

MPL Induces Autophagy

Figure 6:
FIG. 6 shows that treatment of A2780 ovarian cancer cells with MPL or U87 glioma cells with MPL-SO2 lead to the formation of vacuoles suggesting that MPL and MPL-SO2 induce autophagy in these cells.
Figure 6:
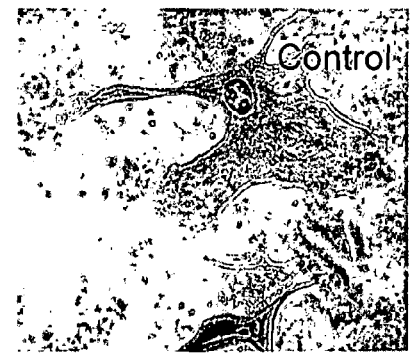
Figure 6:
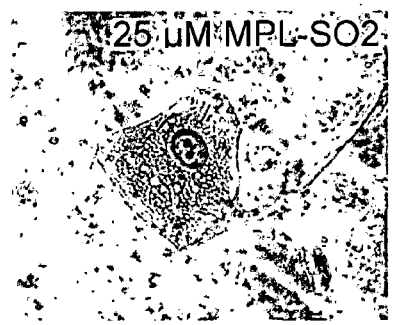
Figure 7:
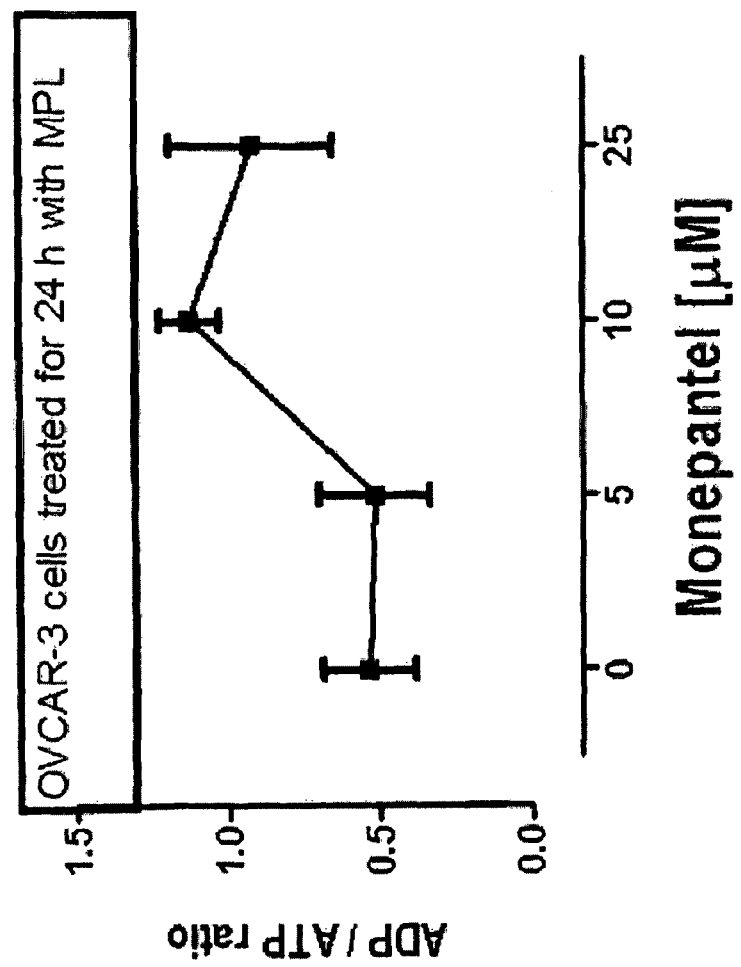
FIG. 7, consistent with that shown in FIG. 6, shows that MPL treatment reduces the cellular ratio of ADP/ATP, which is another indicator of cellular autophagy.

FIG. 6 shows that the treatment of cells with MPL leads to the formation of vacuoles suggesting that MPL may be inducing autophagy in these cells. FIG. 7 shows that MPL treatment reduces the cellular ratio of ADP/ATP, which is another indicator of cellular autophagy.

MPL Suppresses Rate of s.c. Xenografts Growth in Nude Mice

FIGS. 19-21 shows in vivo testing of the MPL in nude mice. Mice bearing OVCAR-3 tumors were treated either first i.p. or, as according to the last experiment, orally. Results obtained reveal the activity of the administered doses and in particular the 50 mg/kg dose (both i.p. and oral) in profoundly retarding tumor growth in these animals. Tumor histology revealed massive areas of tumor cell death (FIG. 22).

The inhibition of cell proliferation coupled with suppression of colony formation, and the in vivo results show a growth regulatory effect for MPL. MPL interference is shown with the cell cycle progression through reducing expression of cell cycle regulatory proteins A and E2 together with their kinases cdk2 and cdk4. In the normal cell, the transition from one phase to another occurs in an orderly fashion well regulated by various proteins. Cyclin-dependent kinases (CDK) are the key regulatory proteins that are activated at specific points of the cell cycle thus playing a crucial role in cell cycle progression. These require different cyclins at different phases of the cycle. Cyclins A, D and E are required for the G1 and G1 transition to S phase of the cell cycle. Of the various CDKs identified so far, CDK2 and CDK4 seem essential for entry in G1 and G1-S transition. Cyclins A and E bind to CDK2 while cyclin D binds to CDK4 and CDK6. Cancer is one of several diseases considered to be a cell cycle related phenomenon.

Results presented in FIGS. 19-21 demonstrate MPL activity in suppressing s.c. tumor growth in female nude mice. The initial trial revealed dose-dependent activity of i.p. MPL administration. The 25 mg/kg dose was particularly effective. On this basis, the next trial was conducted using 25 and 50 mg/kg doses under the same conditions as before. The 50 mg/kg dose was more effective in retarding tumor growth in these animals. As an anti-parasitic agent, MPL has been shown to be orally effective in a number of animal models. The oral therapeutic activity of 50 and 100 mg/kg doses of MPL were tested. In all three pilot trials, MPL was prepared in 0.5% HPMC and administered as a suspension. Examination of tumor tissue from these in vivo trial revealed areas with extensive necrosis in the MPL treated tumors (FIG. 22).

The effects observed are not limited to ovarian cancer, as shown in Tables 1 and 2, and MPL effectively suppresses in vitro cell proliferation in a variety of cell lines representing various cancers including, glioma, prostate, breast, mesothelioma, liposarcoma, fibrosarcoma (see Tables 1 and 2).

Another important observation is the activity of MPL against chemo-resistant cell lines. Ovarian chemo-resistant cells, glioma temozolimide resistant cells and breast cancer tamoxifen resistant cells were all sensitive to MPL antiproliferative action.

In conclusion, the results demonstrate that in cancer cell-lines, MPL and potentially its metabolites and analogues (AADs):

1—Inhibit cell proliferation;
2—MPL-induced inhibition is neither positively nor negatively affected by pre-treatment with nicotinic agonists or antagonists indicating that the mode of action is not nicotine receptor mediated;
2—inhibit colony formation;
3—Arrest cell cycle [G1 phase];
4—Down regulate cell-cycle regulatory proteins (CdK2, CdK4, cyclin A, cyclin E);
5—Blocks thymidine incorporation into the cell thus inhibits DNA synthesis;
6—Reduces cellular ATP levels;
7—Causes progressive autophagy as confirmed by conversion of LC3B-I into LC3B-II;
8—Autophagy was microscopically clear in both ovarian and glioma cancer cell lines;
9—MPL also induces cleavage of PARP-1 and thus cell death;
10—This is confirmed by in vivo data showing dose-dependent suppression of tumors in nude mice bearing s.c. tumors;
11—Both i.p. and oral routes of administration were effective.

Furthermore, MPL inhibits proliferation of cells resistant to some standard chemotherapy.

Discussion

As shown in Table 1, MPL was also tested on HUVECs. It was found that the $IC_{50}$ value is about 10 times higher than the $IC_{50}$ value in OVCAR-3, which reflects the higher cytotoxic potency of MPL on cancerous than non-cancerous cells.

In colony formation assays, MPL suppressed formation of colonies by ovarian cancer cell lines growing on agar plates in a concentration-dependent manner and therefore further demonstrates the efficacy of MPL to inhibit the growth of cancer cells.

In addition, it has been shown that irrespective of the p53 status of the [OVCAR-3 (mutated), SKOV-3 (null) and A2780 (wild type)] cells, MPL exerted its anti-cancer effects (albeit at different potencies). This suggests that MPL would be effective in epithelial ovarian cancers irrespective of their tumor p53 status. This finding may be of importance as p53 mutation is highly common in a wide range of cancers.

It is to be understood that the effects shown by MPL may be extended to other types of cancers in addition to ovarian cancer.

The mammalian cell cycle is governed by sequential activation of the Cdks. Progression through the G1 phase and entry into the S phase is regulated by Cdk2 complexed with cyclin A and cyclin E. Therefore, suppressing the expression of these regulatory proteins disrupts the cell cycle progress.

Inhibition of cell proliferation and colony formation is concentration-dependent on MPL. A possible mechanism by which MPL disrupts cell cycle progression is down-regulation of cell cycle regulatory proteins E and A and the cycline-dependent kinases Cdk4 and Cdk2, causing G1 arrest. As a result of G1 arrest, cells do not progress onto the next stage of the cycle as shown by a dramatic reduction of cells in the S and G2-M phases over time. The percentage of cells in the G2-M phase of the vehicle treated group was more than three times higher than those in the group treated with 25 μM MPL.

Furthermore, the evidence of autophagy in the cancer cell lines treated with MPL strongly suggests that the cells are irreversibly exiting the cell-cycle via a $G_0$ phase cell cycle arrest.

The invention claimed is:

1. A method for the treatment of one or more cancers, the method comprising administering a therapeutically effective amount of a compound of formula (I):

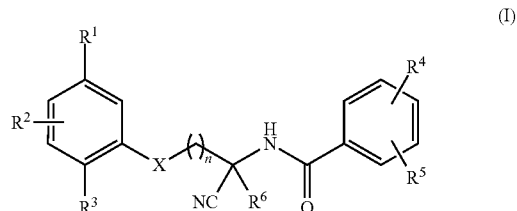

or a pharmaceutically acceptable salt, solvate or prodrug thereof to a patient in need thereof, wherein i) $R^1$ is alkyl, —$CF_3$ or —CN and $R^4$ is selected from H, alkyl, halogen, alkoxy, —$CF_3$, —$OCF_3$, —$SO_2$—$CF_3$, —SO—$CF_3$ or —S—$CF_3$; or ii) $R^4$ is H, alkyl, halogen, alkoxy,—S—$CF_3$, —$SOCF_3$ or —$SO_2CF_3$ and $R^1$ is selected from H, alkyl, halogen, —$CF_3$ or —CN;

$R^2$ and $R^3$ and $R^5$ are each independently selected from H, alkyl, halogen, —$CF_3$ or —CN;

$R^6$ is independently selected from H, alkyl, halogen, alkoxy, —$CF_3$, —$OCF_3$, —$SO_2CF_3$, —SO—$CF_3$ or —S—$CF_3$;

X is heteroatom, N(alkyl) or NH; and n is 1 to 20 wherein the cancer is selected from ovarian cancer, breast cancer, colon cancer, mesothelioma, cervical cancer, prostate cancer, skin cancer, glioma, liposarcoma, fibrosarcoma and leukemia.

2. The method of claim 1, wherein $R^1$ is —CN, H or halogen.

3. The method of claim 1, wherein $R^2$ is H or halogen.

4. The method of claim 1, wherein $R^3$ is —$CF_3$ or halogen.

5. The method of claim 1, wherein $R^4$ is —S—$CF_3$, —$SOCF_3$, —$SO_2CF_3$, —$OCF_3$ or —$CF_3$.

6. The method of claim 1, wherein $R^5$ is H.

7. The method of claim 1, wherein X is O.

8. The method of claim 1, wherein n is 1.

9. The method of claim 1, wherein $R^4$ is *para* to the amide moiety.

10. The method of claim 1, wherein the compound of formula (I) is the (R)— or (S)-enantiomer or the racemate.

11. The method of claim 1, wherein the compound of formula (I) is the (S)-enantiomer.

12. The method of claim 1, wherein the compound of formula (I) is selected from any one of the following compounds:

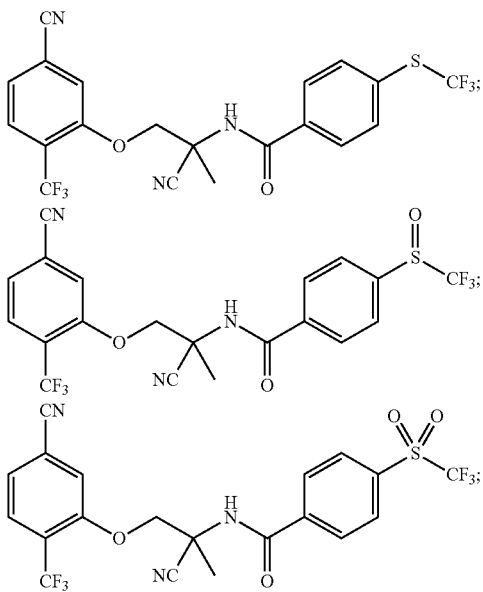

wherein each of the above compounds is the (R)— or (S)-enantiomer, or the racemate, or a pharmaceutically acceptable salt, solvate or prodrug thereof.

13. The method of claim 1, wherein the compound of formula (I) is MPL (N-[(1S)-1-cyano-2-(5-cyano-2-trifluoromethyl-phenoxy)-1-methyl-ethyl]-4-trifluoromethylsulfanyl-benzamide):

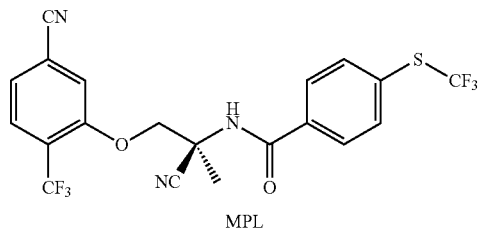 [SMILES: C[C@](C#N)(COc1cc(C#N)ccc1C(F)(F)F)NC(=O)c1ccc(SC(F)(F)F)cc1]

MPL or a metabolite, pharmaceutically acceptable salt, solvate or prodrug thereof, wherein the metabolite is a sulfoxide or sulfone (MPL-SO₂).

14. The method of claim 1, wherein the compound of formula (I) is monepantel sulphone (MPL-SO2):

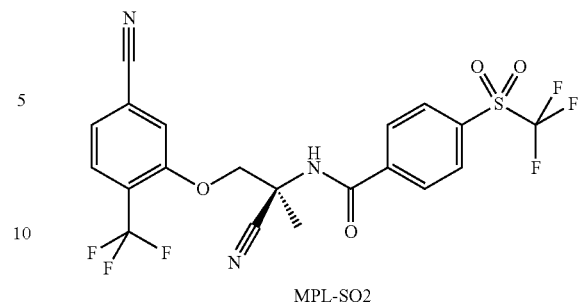

MPL-SO2 or a metabolite, pharmaceutically acceptable salt, solvate or prodrug thereof.

15. The method of claim 1, wherein the compound of formula (I) is:

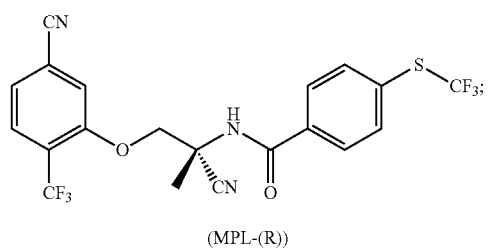

AAD 2224

(MPL-(R))

or a metabolite, pharmaceutically acceptable salt, solvate or prodrug thereof, wherein the metabolite is a sulfoxide or sulfone (MPL-SO₂).

16. The method of claim 1, wherein the cancer is selected from ovarian cancer, breast cancer, colon cancer, glioma or mesothelioma.

17. The method of claim 1, wherein the cancer is ovarian cancer.

18. The method of claim 1, wherein the therapeutically effective amount of a compound according to formula (I) is administered in a pharmaceutical composition comprising at least one pharmaceutically acceptable carrier.

19. The method of claim 1, wherein the leukemia is myeloid leukemia.

20. The method of claim 19, wherein the myeloid leukemia is acute promyelocytic leukemia or chronic myelogenous leukemia.

* * * * *